United States Patent
Nakamura et al.

(10) Patent No.: US 11,136,361 B2
(45) Date of Patent: Oct. 5, 2021

(54) FUSION PROTEIN FOR IMPROVING PROTEIN EXPRESSION FROM TARGET MRNA

(71) Applicant: KYUSHU UNIVERSITY, NATIONAL UNIVERSITY CORPORATION, Fukuoka (JP)

(72) Inventors: Takahiro Nakamura, Fukuoka (JP); Yusuke Yagi, Fukuoka (JP)

(73) Assignee: KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 259 days.

(21) Appl. No.: 16/305,080

(22) PCT Filed: May 30, 2017

(86) PCT No.: PCT/JP2017/020076
§ 371 (c)(1),
(2) Date: Nov. 28, 2018

(87) PCT Pub. No.: WO2017/209122
PCT Pub. Date: Dec. 7, 2017

(65) Prior Publication Data
US 2019/0309029 A1    Oct. 10, 2019

Related U.S. Application Data

(60) Provisional application No. 62/345,252, filed on Jun. 3, 2016.

(30) Foreign Application Priority Data

Jun. 17, 2016   (JP) .............................. JP2016-120524

(51) Int. Cl.
| | | |
|---|---|---|
| C07K 14/415 | (2006.01) | |
| C07K 14/435 | (2006.01) | |
| C12N 15/62 | (2006.01) | |
| C12N 15/85 | (2006.01) | |
| C07K 19/00 | (2006.01) | |

(52) U.S. Cl.
CPC .......... *C07K 14/415* (2013.01); *C07K 14/435* (2013.01); *C07K 19/00* (2013.01); *C12N 15/62* (2013.01); *C12N 15/85* (2013.01); *C07K 2319/04* (2013.01); *C07K 2319/06* (2013.01); *C07K 2319/81* (2013.01); *C12N 2310/20* (2017.05)

(58) Field of Classification Search
CPC C07K 14/415; C07K 14/435; C07K 16/2818; C07K 16/2827; C07K 16/2863; C07K 19/00; C07K 2319/04; C07K 2319/06; C07K 2319/81; C12N 15/8261; C12N 15/8271; C12N 15/8273; C12N 15/8247; C12N 15/827; C12N 15/62; C12N 15/8242; C12N 15/85; C12N 2310/20; Y02A 40/146; A61K 39/39558; G06F 11/00
See application file for complete search history.

(56) References Cited

U.S. PATENT DOCUMENTS

| | | | | |
|---|---|---|---|---|
| 7,531,300 | B2* | 5/2009 | Nakamura | .............. A61P 35/00 435/4 |
| 8,044,193 | B2* | 10/2011 | Nakamura | ........... C12Q 1/6886 536/24.5 |
| 9,513,283 | B2* | 12/2016 | Nakamura | ........... C07K 14/415 |
| 2007/0269432 | A1* | 11/2007 | Nakamura | .............. A61P 35/04 424/138.1 |
| 2009/0286856 | A1* | 11/2009 | Nakamura | ....... G01N 33/57415 514/44 R |
| 2012/0010090 | A1* | 1/2012 | Nakamura | ........... C12Q 1/6886 506/7 |
| 2013/0004991 | A1 | 1/2013 | Cosson et al. | |
| 2014/0335521 | A1 | 11/2014 | Nakamura et al. | |
| 2016/0075744 | A1 | 3/2016 | Yamamoto et al. | |
| 2016/0281129 | A1 | 9/2016 | Kim et al. | |

FOREIGN PATENT DOCUMENTS

| | | |
|---|---|---|
| JP | 2006-217871 | 8/2006 |
| JP | 2007159567 A | 6/2007 |
| JP | 2009544296 A | 12/2009 |
| JP | 2015-221026 | 12/2015 |
| WO | 2011/111828 | 9/2011 |
| WO | 2013058404 A1 | 4/2013 |
| WO | 2015056762 A1 | 4/2015 |

OTHER PUBLICATIONS

Woodson JD et al. Coordination of gene expression between organellar and nuclear genomes. Nat Rev Genet. 2008; 9(5): 383-395.
(Continued)

*Primary Examiner* — Marcela M Cordero Garcia
(74) *Attorney, Agent, or Firm* — Myers Bigel, P.A.

(57) ABSTRACT

[Problem to be Solved] The object of the present invention is to develop a method of regulating a target RNA.
[Solution] There is provided a fusion protein comprising a functional domain which improves the protein expression level from mRNA and a PPR protein which can bind to a target mRNA in an RNA base-selective or RNA base sequence-specific manner.

19 Claims, 6 Drawing Sheets

Specification includes a Sequence Listing.

(56) References Cited

OTHER PUBLICATIONS

Cans, Christophe, et al., "Translationally controlled tumor protein acts as a guanine nucleotide dissociation inhibitor on the translation elongation factor eEF1A", PNAS, 100(24):13892-13897 (2003).
Pérez-Arellano, Isabel, et al., "Human Drg1 is a potassium-dependent GTPase enhanced by Lerepo4", The FEBS Journal, 280(15):3647-3657 (2013).
Sakaguchi, Masao, "Membrane Integration and Folding of Membrane Proteins via Endoplasmic Reticulum Translocon", Membrane, 35(2):63-71 (2010) (English Abstract).
Skabkin, Maxim A., et al., "Activities of Ligatin and MCT-1/DENR in eukaryotic translation initiation and ribosomal recycling", Genes & Development, 24(16):1787-1801 (2010).
Whitfield, Michael L., et al., "Stem-Loop Binding Protein, the Protein That Binds the 39 End of Histone mRNA, Is Cell Cycle Regulated by Both Translational and Posttranslational Mechanisms", Molecular and Cellular Biology, 20(12):4188-4198 (2000).
Japanese Office Action corresponding to JP 2018-520924, dated Mar. 1, 2021 (10 pages, including English translation).

\* cited by examiner

[Figure 1]
A Effector plasmid
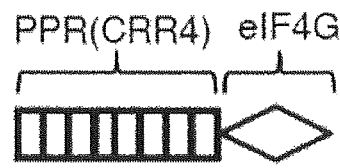
Reporter plasmid
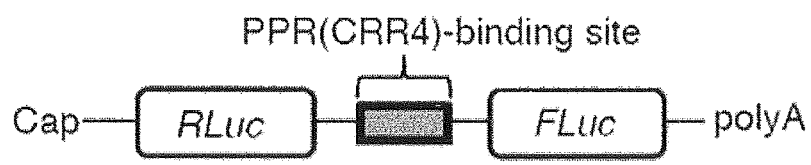
B
Binding sequence
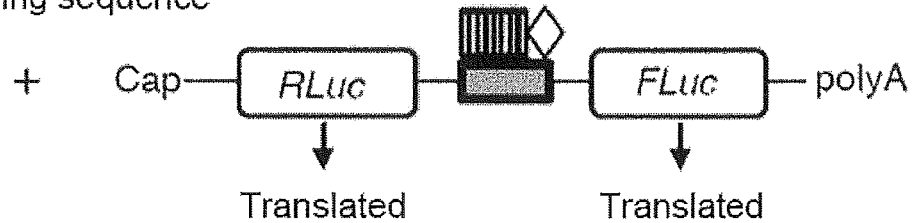
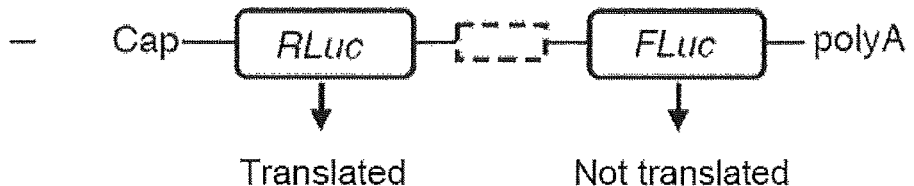

[Figure 2]
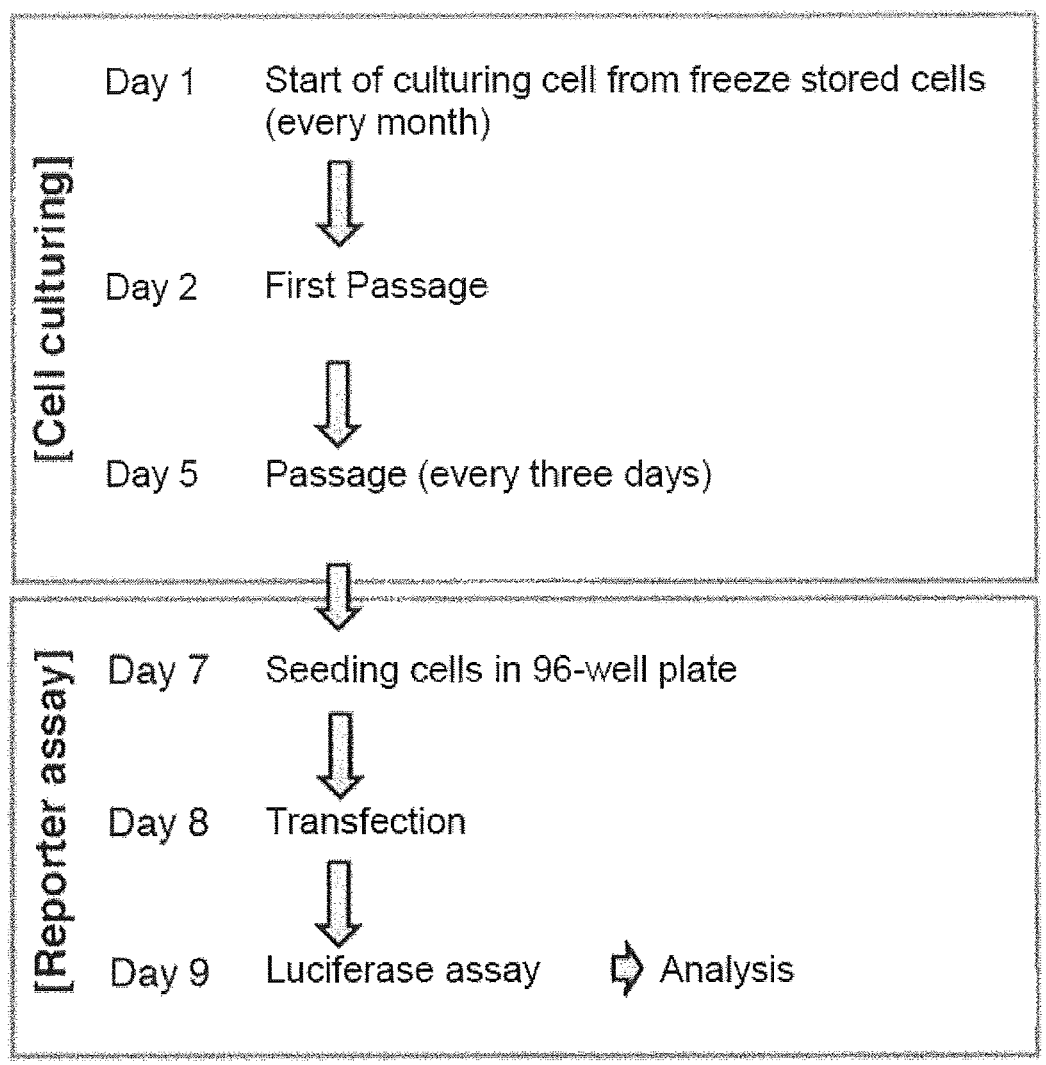

[Figure 3]
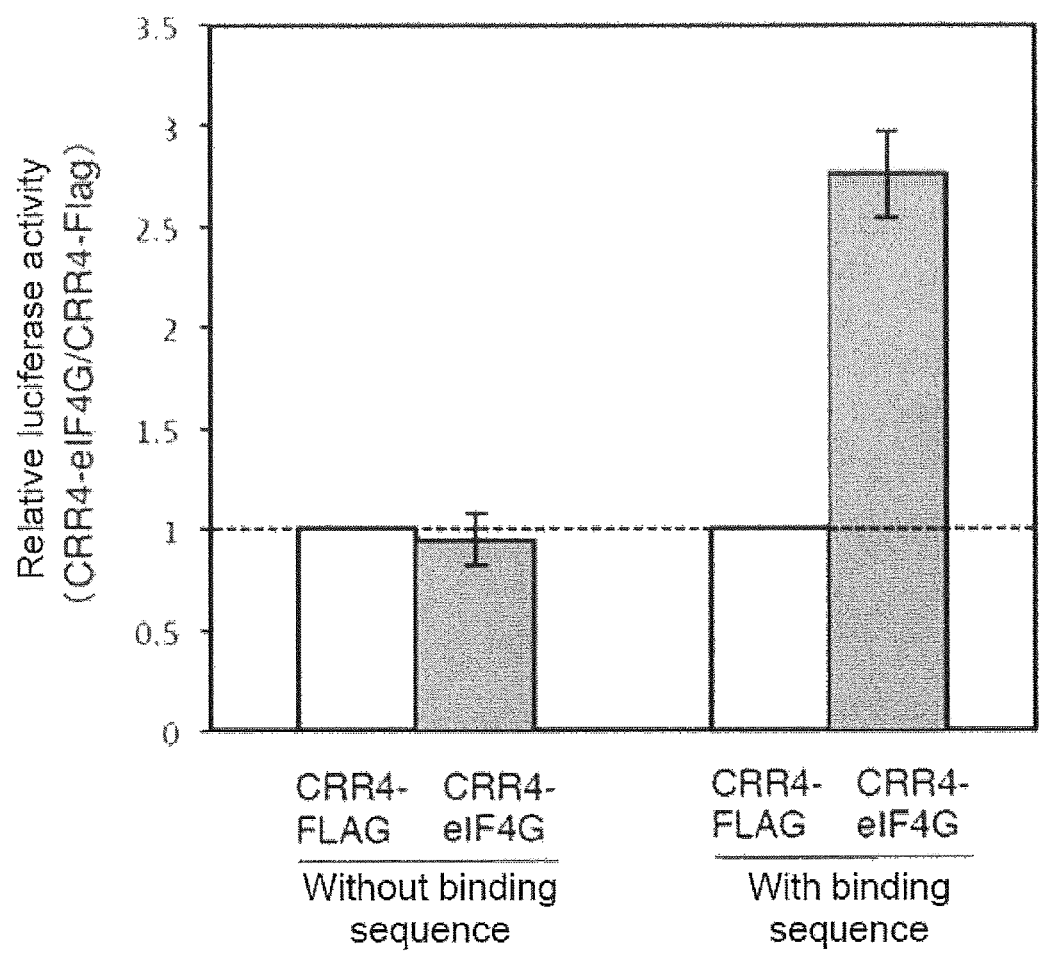

[Figure 4]
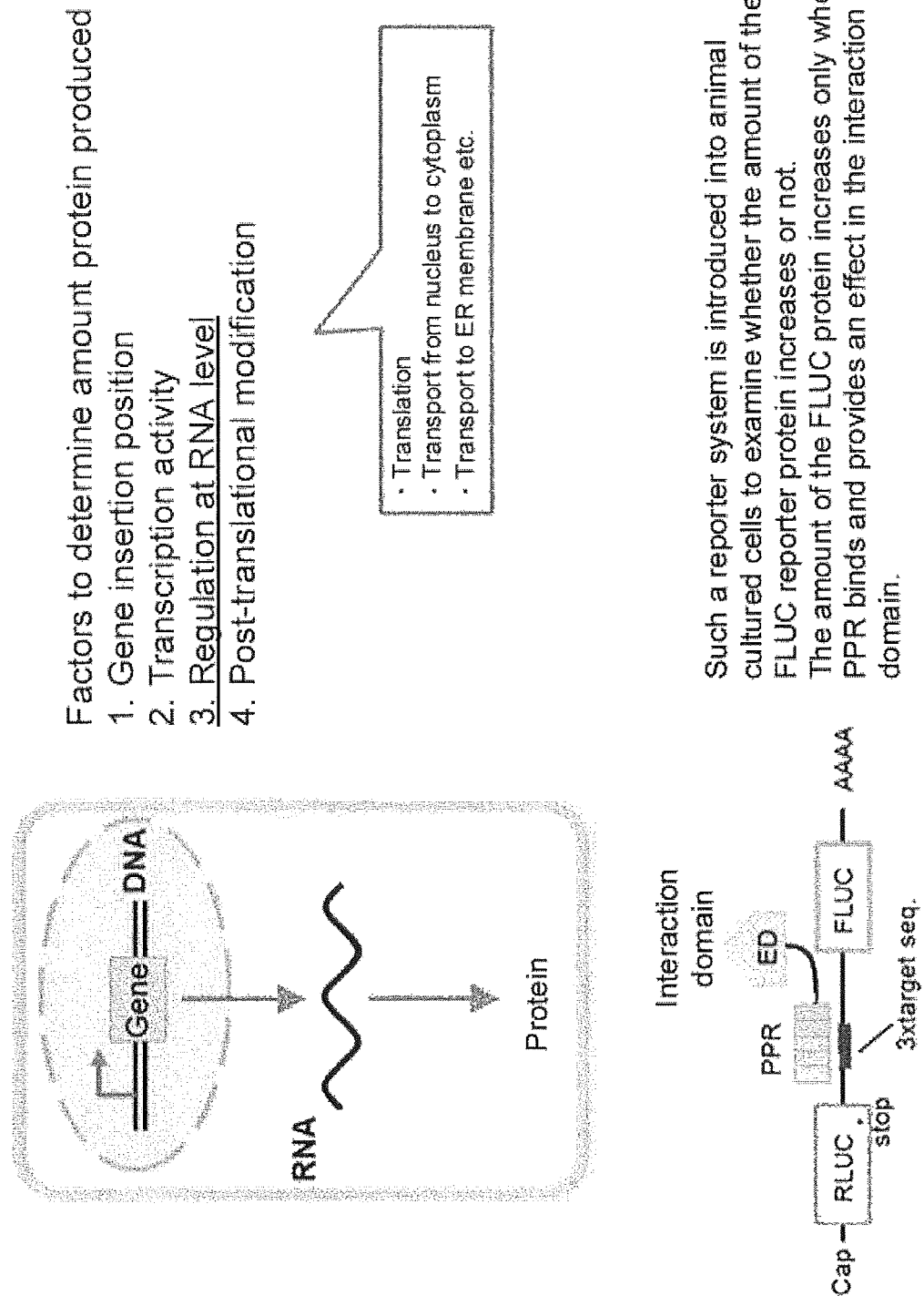

[Figure 5]
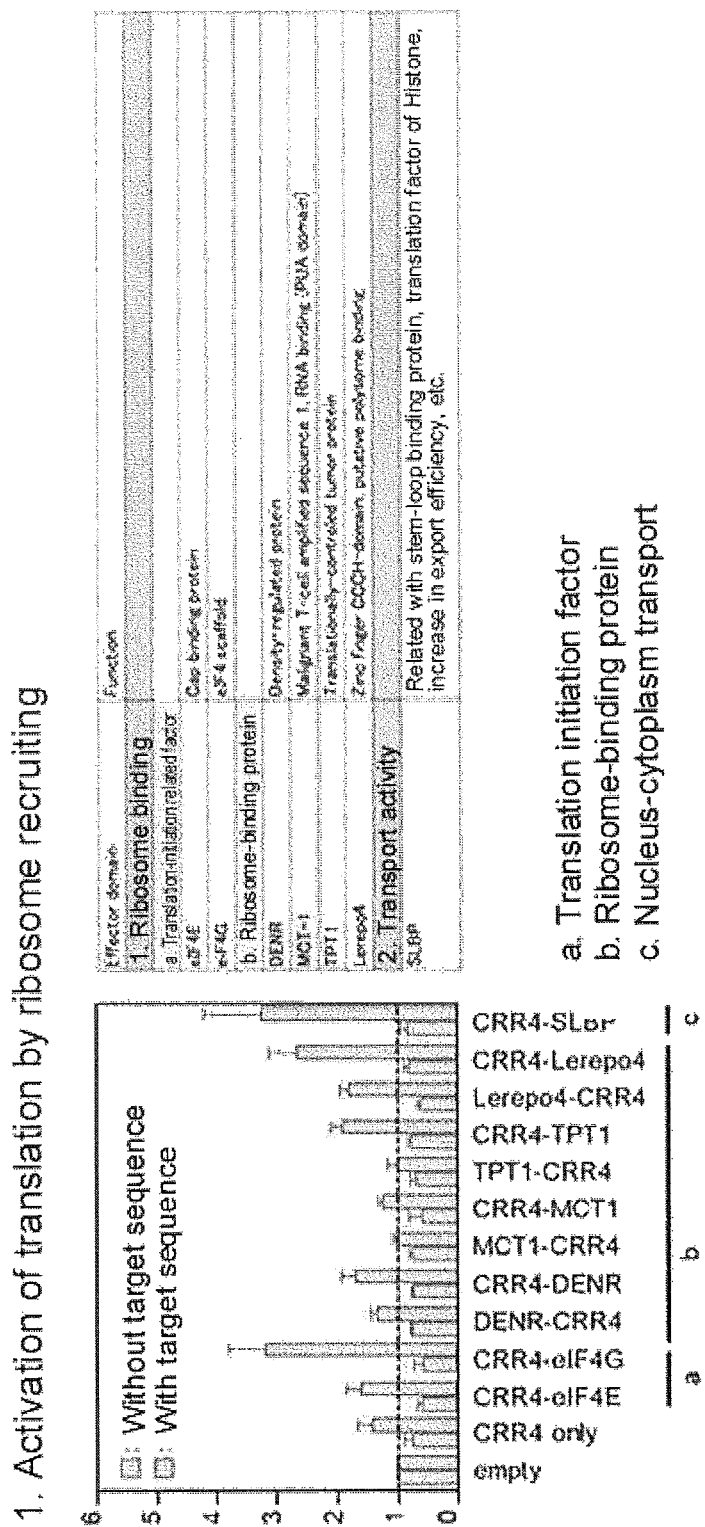

[Figure 6]
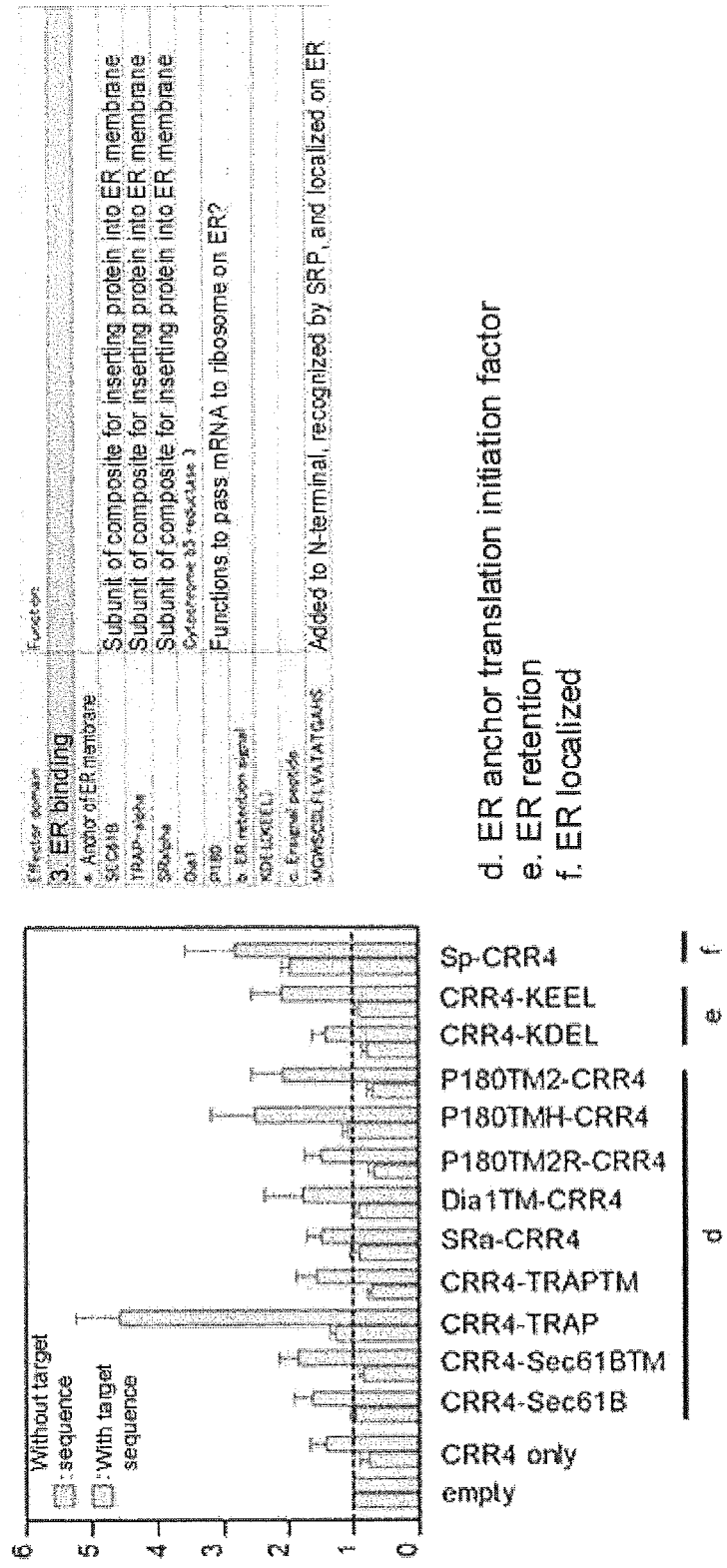

FUSION PROTEIN FOR IMPROVING PROTEIN EXPRESSION FROM TARGET MRNA

STATEMENT OF PRIORITY

This application is a 35 U.S.C. § 371 of national phase entry of International Application Serial No. PCT/JP2017/020076, tied May 30, 2017, which claims the benefit, under 35 U.S.C. § 119(a) of U.S. Provisional Application No. 62/345,252, flied Jun. 3, 2016, and of Japanese Patent Application No. 2016-120524, filed Jun. 17, 2016, the entire contents of each of which are Incorporated herein by reference herein.

TECHNICAL FIELD

The present invention relates to fusion proteins for improving protein expression levels from target mRNAs.

BACKGROUND ART

Techniques of binding nucleic acid-binding protein factors revealed by a variety of analyses to sequences of interest are established and used in recent years. Use of this sequence-specific binding enables removal of a target DNA sequence or regulation (activation or inactivation) of expression of a protein coding gene present downstream of the target DNA sequence in some extent.

While zinc finger nuclease (ZFN), TAL effector nuclease (TALEN), Crispr-cas9, and the like are known as techniques using protein factors which act on DNA, the development of techniques using protein factors which act specifically to RNA is still limited.

The present inventors have proposed a method of designing a protein which can specifically bind to a target RNA sequence using the properties of PPR proteins (protein having one or more pentatricopeptide repeat (PPR) motifs), which are proteins mainly found in plants (Patent Literature 1).

CITATION LIST

Patent Literature

[Patent Literature 1]
WO2013/058404

SUMMARY OF INVENTION

Technical Problem

In the disclosure according to Patent Literature 1, the amino acids which function when a PPR motif demonstrates RNA-binding properties were identified, and the relation between the structure of the PPR motif and the target base was revealed, thereby enabling the construction of proteins which have one or more PPR motifs and can bind to RNAs having any sequence and length. However, no method has ever been found which actually regulates target RNAs using the techniques according to Patent Literature 1.

Solution to Problem

As a result of extensive research on a method of improving a protein expression level from a target mRNA using a PPR protein, the present inventors have found that a fusion protein of a predetermined functional domain and a PPR protein improves the protein expression level from the target mRNA, and have completed the present invention.

Specifically, an embodiment of the present invention relates to a fusion protein for improving a protein expression level from a target mRNA, the fusion protein comprising:

(A) one or more functional domains which improve a protein expression level from an mRNA; and (B) a polypeptide moiety which can bind to a target mRNA in an RNA base-selective or RNA base sequence-specific manner, wherein polypeptide moiety (B) is a polypeptide moiety comprising one or more PPR motifs, each PPR motif comprising a polypeptide consisting of 30 to 38 amino acids in length and being represented by Formula 1:

[Formula 1]

$$(\text{Helix A})\text{-X-}(\text{Helix B})\text{-L} \qquad \text{(Formula 1)}$$

where

Helix A is a moiety which consists of 12 amino acids in length and can form an α-helix structure, and is represented by Formula 2:

[Formula 2]

$$A_1\text{-}A_2\text{-}A_3\text{-}A_4\text{-}A_5\text{-}A_6\text{-}A_7\text{-}A_8\text{-}A_9\text{-}A_{10}\text{-}A_{11}\text{-}A_{12} \qquad \text{(Formula 2)}$$

where $A_2$ to $A_{12}$ each independently represent an amino acid;

X is not present, or is a moiety consisting of 1 to 9 amino acids in length;

Helix B is a moiety which consists of 11 to 13 amino acids in length and can form an α-helix structure;

L is a moiety consisting of 2 to 7 amino acids in length and represented by Formula 3:

[Formula 3]

$$L_{vii}\text{-}L_{vi}\text{-}L_{v}\text{-}L_{iv}\text{-}L_{iii}\text{-}L_{ii}\text{-}L_{i} \qquad \text{(Formula 3)}$$

where the amino acids are numbered from the C-terminal as "i" (−1), "ii" (−2), . . . and $L_{iii}$ to $L_{vii}$ may not be present, and a combination of three amino acids $A_1$, $A_4$, and $L_{ii}$ or a combination of two amino acids $A_4$ and $L_{ii}$ corresponds to a base or base sequence of the target mRNA.

In an embodiment according to the present invention, polypeptide moiety (B) comprises 2 to 30 PPR motifs, and the plurality of PPR motifs is arranged so as to specifically bind to the base sequence of the target mRNA.

Moreover, in an embodiment according to the present invention, polypeptide moiety (B) comprises 5 to 25 PPR motifs.

Moreover, in an embodiment according to the present invention, one or more functional domains (A) each bind to an N-terminal side and/or a C-terminal side of polypeptide moiety (B).

Moreover, in an embodiment according to the present invention, one or more functional domains (A) are selected from the group consisting of a domain which guides ribosome to the mRNA, a domain associated with initiation or promotion of translation of the mRNA, a domain associated with nuclear export of the mRNA, a domain associated with binding to an endoplasmic reticulum membrane, a domain containing an endoplasmic reticulum retention signal (ER retention signal) sequence, and a domain containing an endoplasmic reticulum signal sequence.

Moreover, in an embodiment according to the present invention, the domain which guides ribosome to the mRNA is a domain containing all or functional part of a polypeptide selected from the group consisting of DENR (Density-regulated protein), MCT-1 (Malignant T-cell amplified sequence 1), TPT1 (Translationally-controlled tumor protein), and Lerepo4 (Zinc finger CCCH-domain), the domain associated with initiation or promotion of translation of the mRNA is a domain containing all or functional part of a polypeptide selected from the group consisting of eIF4E and eIF4G, the domain associated with nuclear export of the mRNA is a domain containing all or functional part of SLBP (Stem-loop binding protein), the domain associated with binding to an endoplasmic reticulum membrane is a domain containing all or functional part of a polypeptide selected from the group consisting of SEC61B, TRAP-alpha (Translocon associated protein alpha), SR-alpha, Dial (Cytochrome b5 reductase 3), and p180, the endoplasmic reticulum retention signal (ER retention signal) sequence is a signal sequence containing a KDEL (SEQ ID NO:20)(KEEL) (SEQ ID NO:21) sequence, or the endoplasmic reticulum signal sequence is a signal sequence containing MGWSCIILFLVATATGAHS (SEQ ID NO: 22).

Moreover, in an embodiment according to the present invention, the combination of the three amino acids $A_1$, $A_4$, and $L_{ii}$ in each of the PPR motifs is:

(valine, threonine, asparagine), (phenylalanine, serine, asparagine), (phenylalanine, threonine, asparagine), (isoleucine, asparagine, aspartic acid), or (threonine, threonine, asparagine) in order of ($A_2$, $A_4$, $L_{ii}$) if a target base for the PPR motif is A (adenine);

(glutamic acid, glycine, aspartic acid), (valine, threonine, aspartic acid), (lysine, threonine, aspartic acid), or (leucine, threonine, aspartic acid) in order of ($A_1$, $A_4$, $L_{ii}$) if the target base for the PPR motif is G (guanine);

(valine, asparagine, aspartic acid), (isoleucine, asparagine, asparagine), (isoleucine, asparagine, aspartic acid), (isoleucine, methionine, aspartic acid), (phenylalanine, proline, aspartic acid), or (tyrosine, proline, aspartic acid) in order of ($A_1$, $A_4$, $L_{ii}$) if the target base for the PPR motif is U (uracil); or (valine, asparagine, asparagine), (isoleucine, asparagine, asparagine), (valine, asparagine, serine), or (isoleucine, methionine, aspartic acid) in order of ($A_1$, $A_4$, $L_{ii}$) if the target base for the PPR motif is C (cytosine).

Moreover, in an embodiment according to the present invention, the combination of the two amino acids $A_4$ and $L_{ii}$ in each of the PPR motifs is:

(threonine, asparagine), (serine, asparagine), or (glycine, asparagine) in order of ($A_4$, $L_{ii}$) if a target base for the PPR motif is A (adenine);

(threonine, aspartic acid) or (glycine, aspartic acid) in order of ($A_4$, $L_{ii}$) if the target base for the PPR motif is G (guanine);

(asparagine, aspartic acid), (proline, aspartic acid), (methionine, aspartic acid), or (valine, threonine) in order of ($A_4$, $L_{ii}$) if the target base for the PPR motif is U (uracil); or (asparagine, asparagine), (asparagine, serine), or (leucine, aspartic acid) in order of ($A_4$, $L_{ii}$) if the target base for the PPR motif is C (cytosine).

Another embodiment according to the present invention relates to a nucleic acid which encodes the fusion protein according to the present invention.

Still another embodiment according to the present invention relates to a vector (preferably an expression vector) comprising the nucleic acid according to the present invention.

Further still another embodiment according to the present invention relates to a method of improving a protein expression level from a target mRNA within a cell, the method comprising:

a step of providing the fusion protein according to the present invention or the vector according to the present invention; and a step of introducing the fusion protein or the vector into the cell.

Moreover, in an embodiment according to the present invention, the cell is a eukaryotic cell.

Moreover, in an embodiment according to the present invention, the cell is an animal cell.

Moreover, in an embodiment according to the present invention, the animal cell is a human cell.

Inventions having any combination of one or more features of the present invention described above are also included in the scope of the present invention.

BRIEF DESCRIPTION OF DRAWINGS

FIG. 1 illustrates a schematic view of an effector plasmid and a reporter plasmid used in Examples, and a schematic view of an experimental outline. FIG. 1A illustrates a schematic view of the effector plasmid and the reporter plasmid used in Examples. A fusion protein of PPR motifs and eIF4G expresses from the effector plasmid. In Examples, a CRR4 protein was used, whose target sequence is well researched. From the reporter plasmid, renilla luciferase (RLuc) and firefly luciferase (FLuc) are transcribed in the form of a dicistronic mRNA. A PPR-binding sequence (here, CRR4-binding sequence) was inserted into a site on the 5' end of FLuc. FIG. 1B illustrates a schematic view of an experimental outline of Examples. Irrespective of the presence/absence of the PPR-binding sequence, RLuc is translated at a similar level. For this reason, the activity value of RLuc can be treated as a control in transfection in this reporter system. The translation of Fluc is started only when PPR-eIF4G binds to the PPR-binding sequence and translation factors can be attracted by the effects of eIF4G. In contrast, the translation of FLuc remains at a low level if the PPR-binding sequence is not present and thus, PPR-eIF4G cannot bind to the PPR-binding sequence.

FIG. 2 illustrates an experimental procedure of a reporter assay using HEK293T cells.

FIG. 3 shows the experimental results of Example 1. The activation of sequence-specific translation depends on CRR4-eIF4G and the PPR-binding sequence. This experiment was performed using an effector plasmid, into which CRR4-Flag (without translation activating factor, in white) or CRR4-eIF4G (with translation activating factor, in gray) was inserted, and a reporter vector with or without an inserted PPR-binding sequence. From the results, it was verified that specific translation activity increased 2.75 times in the presence of both PPR-eIF4G and the PPR-binding sequence. The value represents the average and the standard deviation (N=3).

FIG. 4 illustrates an outline of the experiment in Example 2.

FIG. 5 illustrates the experimental results in Example 2 and the functions of the domains.

FIG. 6 illustrates the experimental results in Example 2 and the functions of the domains.

DESCRIPTION OF EMBODIMENT

[PPR Motifs and PPR Proteins]

Unless otherwise specified, the term "PPR motif" used in the present invention indicates a polypeptide which is composed of 30 to 38 amino acids and has an amino acid sequence having an E value equal to or less than a predetermined value (desirably E-03), the E value being obtained at PF01535 in Pfam and PS51375 at Prosite during the analysis of the amino acid sequence with a protein domain search program on the Web. The position number of an amino acid forming the PPR motif defined in the present invention is substantially as defined as PF01535 while it corresponds to the number obtained by subtracting 2 from the location of the amino acid in PS51375 (for example, position 1 in the present invention corresponds to position 3 in PS51375). Note that the term "ii" (−2)-th amino acid refers to the second amino acid from the tail end (C-terminal side) of the amino acids forming one PPR motif or the amino acid close to the N-terminal by two amino acids from the first amino acid of the next PPR motif (that is, −2 amino acid). If the next PPR motif is not clearly identified, the forward amino acid by two amino acids from the first amino acid of the next helix structure is defined as "ii". See http://pfam.sanger.ac.uk/ for Pfam and http://www.expasy.org/prosite/ for Prosite.

Although the conserved amino acid sequence of the PPR motif has low conservation properties at the amino acid level, two α-helices are well conserved on the secondary structure. Although a typical PPR motif is composed of 35 amino acids, its length is variable from 30 to 38 amino acids.

More specifically, the term PPR motif used in the present invention is composed of a polypeptide having 30 to 38 amino acids in length and being represented by Formula 1:
[Formula 4]

(Helix A)-X-(Helix B)-L    (Formula 1)

where

Helix A is a moiety which consists of 12 amino acids in length and can form an α-helix structure, and is represented by Formula 2:
[Formula 5]

$A_1-A_2-A_3-A_4-A_5-A_6-A_7-A_8-A_9-A_{10}-A_{11}-A_{12}$    (Formula 2)

where $A_1$ to $A_{12}$ each independently represent an amino acid;

X is not present, or is a moiety consisting of 1 to 9 amino acids in length;

Helix B is a moiety which consists of 11 to 13 amino acids in length and can form the α-helix structure; and L is a moiety consisting of 2 to 7 amino acids in length and represented by Formula 3:
[Formula 6]

$L_{vii}-L_{vi}-L_{v}-L_{iv}-L_{iii}-L_{ii}-L_{i}$    (Formula 3)

where the amino acids are numbered from the C-terminal side as "i" (−1), "ii" (−2), . . . and $L_{iii}$ to $L_{vii}$ may not be present.

Unless otherwise specified, the term "PPR protein" used in the present invention indicates a PPR protein comprising one or more PPR motifs described above, preferably two or more PPR motifs described above. Unless otherwise specified, the term "protein" used herein generally indicates substances consisting of polypeptides (chains of several amino acids bound through peptide bond), also including those consisting of relatively low molecular weight polypeptides. The term "amino acid" used in the present invention may indicates a usual amino acid molecule, or otherwise may indicate an amino acid residue forming a peptide chain in some cases. Persons skilled in the art clearly understand from contexts which case the term indicates.

Unless otherwise specified, the "selective" used in the present invention about the binding properties of the PPR motif to the RNA bases indicates that the binding activity of a PPR motif to one of the RNA bases is higher than the binding activity thereof to other bases. Persons skilled in the art can plan the experiment for this selectivity and verify it, and can also determine through calculation.

Unless otherwise specified, the term "RNA base" used in the present invention indicates a base of a ribonucleotide forming an RNA, specifically adenine (A), guanine (G), cytosine (C), or uracil (U). Note that although the PPR protein can have selectivity to the base in the RNA, it does not bind to a nucleic acid monomer.

PPR protein is present in many plants, and 500 proteins, about 5000 motifs can be found in *Arabidopsis thaliana*. PPR motifs and PPR proteins having a variety of amino acid sequences are also present in many land plants such as *Oryza, Populus*, and *Selaginella tamariscina*. In the present invention, PPR motifs and PPR proteins present in the natural world may be used, or PPR motifs and PPR proteins designed based on the method disclosed in WO2013/058404, for example, may be used. Specifically, desired PPR motifs and PPR proteins can be designed based on the following information disclosed in WO2013/058404.

(I) Information on the Position of the Amino Acid Essential for Selective Binding The combination (A1, A4, Lii) of three, i.e., 1st, 4th, and "ii" (−1)-th amino acids of a PPR motif or the combination (A4, Lii) of two, i.e., 4th and "ii" (−1)-th amino acids is essential for selective binding to the RNA base, and the target RNA base for binding can be determined by these combinations.

The present invention can use the findings about the combination of three amino acids A1, A4, and Lii, and/or the combination of two amino acids A4 and Lii disclosed in WO2013/058404.

(II) Information about the Correspondence of the Combination of Three Amino Acids A1, A4, and Lii to RNA Bases (3-1) If the combination of three amino acids A1, A4, and Lii is valine, asparagine, and aspartic acid in this order, the PPR motif has a selective RNA base binding ability as follows: binding to U is the strongest, and binding to C is the second strongest, followed by binding to A or G.

(3-2) If the combination of three amino acids A1, A4, and Lii is valine, threonine, and asparagine in this order, the PPR motif has a selective RNA base binding ability as follows: binding to A is the strongest, and binding to G is the second strongest, followed by binding to C without binding to U.

(3-3) If the combination of three amino acids A1, A4, and Lii is valine, asparagine, and asparagine in this order, the PPR motif has a selective RNA base binding ability as follows: binding to C is the strongest and binding to A or U is the second strongest, without binding to G.

(3-4) If the combination of three amino acids A1, A4, and Lii is glutamic acid, glycine, and aspartic acid in this order, the PPR motif has a selective RNA base binding ability as follows: binding to G is strong, without binding to A, U, or C.

(3-5) If the combination of three amino acids A1, A4, and Lii is isoleucine, asparagine, and asparagine in this order, the PPR motif has a selective RNA base binding ability as follows: binding to C is the strongest, and binding to U is the second strongest, followed by binding to A, without binding to G.

(3-6) If the combination of three amino acids A1, A4, and Lii is valine, threonine, and aspartic acid in this order, the PPR motif has a selective RNA base binding ability as follows: binding to G is the strongest and binding to U is the second strongest, without binding to A or C.
(3-7) If the combination of three amino acids A1, A4, and Lii is lysine, threonine, and aspartic acid in this order, the PPR motif has a selective RNA base binding ability as follows: binding to G is the strongest and binding to A is the second strongest, without binding to U or C.
(3-8) If the combination of three amino acids A1, A4, and Lii is phenylalanine, serine, and asparagine in this order, the PPR motif has a selective RNA base binding ability as follows: binding to A is the strongest, and binding to C is the second strongest, followed by binding to G and U.
(3-9) If the combination of three amino acids A1, A4, and Lii is valine, asparagine, and serine in this order, the PPR motif has a selective RNA base binding ability as follows: binding to C is the strongest and binding to U is the second strongest, without binding to A or G.
(3-10) If the combination of three amino acids A1, A4, and Lii is phenylalanine, threonine, and asparagine in this order, the PPR motif has a selective RNA base binding ability as follows: binding to A is strong, without binding to G, U, or C.
(3-11) If the combination of three amino acids A1, A4, and Lii is isoleucine, asparagine, aspartic acid in this order, the PPR motif has a selective RNA base binding ability as follows: binding to U is the strongest and binding to A is the second strongest, without binding to G or C.
(3-12) If the combination of three amino acids A1, A4, and Lii is threonine, threonine, and asparagine in this order, the PPR motif has a selective RNA base binding ability as follows: binding to A is strong, without binding to G, U, or C.
(3-13) If the combination of three amino acids A1, A4, and Lii is isoleucine, methionine, and aspartic acid in this order, the PPR motif has a selective RNA base binding ability as follows: binding to U is the strongest and binding to C is the second strongest, without binding to A or G.
(3-14) If the combination of three amino acids A1, A4, and Lii is phenylalanine, proline, and aspartic acid in this order, the PPR motif has a selective RNA base binding ability as follows: binding to U is the strongest and binding to C is the second strongest, without binding to A or G.
(3-15) If the combination of three amino acids A1, A4, and Lii is tyrosine, proline, and aspartic acid in this order, the PPR motif has a selective RNA base binding ability as follows: binding to U is strong, without binding to A, G, or C.
(3-16) If the combination of three amino acids A1, A4, and Lii is leucine, threonine, and aspartic acid in this order, the PPR motif has a selective RNA base binding ability as follows: binding to G is strong, without binding to A, U, or C.
(II) Information about the Correspondence of the Combination of Two Amino Acids A4 and Lii to the RNA Bases
(2-1) If A4 and Lii in this order are asparagine and aspartic acid, the PPR motif has a selective RNA base binding ability as follows: binding to U is the strongest, and binding to C is the second strongest, followed by binding to A and G.
(2-2) If A4 and Lii in this order are asparagine and asparagine, the PPR motif has a selective RNA base binding ability as follows: binding to C is the strongest, binding to U is the second strongest, followed by binding to A and G.
(2-3) If A4 and Lii in this order are threonine and asparagine, the PPR motif has a selective RNA base binding ability with strong binding to A and weak binding to G, U, and C.
(2-4) If A4 and Lii in this order are threonine and aspartic acid, the PPR motif has a selective RNA base binding ability with strong binding to G and weak binding to A, U, and C.
(2-5) If A4 and Lii in this order are serine and asparagine, the PPR motif has a selective RNA base binding ability as follows: binding to A is the strongest and binding to G, U, and C is the second strongest.
(2-6) If A4 and Lii in this order are glycine and aspartic acid, the PPR motif has a selective RNA base binding ability as follows: binding to G is the strongest, and binding to U is the second strongest, followed by binding to A, without binding to C.
(2-7) If A4 and Lii in this order are asparagine and serine, the PPR motif has a selective RNA base binding ability as follows: binding to C is the strongest, and binding to U is the second strongest, followed by binding to A and G.
(2-8) If A4 and Lii in this order are proline and aspartic acid, the PPR motif has a selective RNA base binding ability as follows: binding to U is the strongest, and binding to G, C, and C is the second strongest, without binding to A.
(2-9) If A4 and Lii in this order are glycine and asparagine, the PPR motif has a selective RNA base binding ability as follows: binding to A is the strongest, and binding to G is the second strongest, without binding to C or U.
(2-10) If A4 and Lii in this order are methionine and aspartic acid, the PPR motif has a selective RNA base binding ability with strong binding to U and weak binding to A, G, and C.
(2-11) If A4 and Lii in this order are leucine and aspartic acid, the PPR motif has a selective RNA base binding ability as follows: binding to C is the strongest, and binding to U is the second strongest, without binding to A or G.
(2-12) If A4 and Lii in this order are valine and threonine, the PPR motif has a selective RNA base binding ability as follows: binding to U is the strongest, and binding to A is the second strongest, without binding to G or C.

[Use of PPR Motifs and PPR Proteins]
Identification and Design:
One PPR motif can recognize a specific base of an RNA. According to the present invention, PPR motifs selective to A, U, G, or C can be selected or designed by disposing appropriate amino acids in specific positions of a PPR motif. Furthermore, a protein containing an appropriate series of such PPR motifs can recognize its corresponding specific sequence. Moreover, according to the findings described above, a PPR motif which can selectively bind to a desired RNA base and a protein having a plurality of PPR motifs which can sequence-specifically bind to a desired RNA can be designed. In design, the sequence information of a naturally occurring PPR motif may be referred with respect to moieties other than the amino acids disposed in the important positions of the PPR motif. Alternatively, a PPR motif may be designed by using a naturally occurring PPR motif as a whole and replacing only the amino acids in the important positions with other amino acids. The repetition number of the PPR motif can be appropriately determined according to the target sequence; for example, the repetition number can be 2 or more, or 2 to 30.

The PPR motif or PPR protein thus designed can be prepared by a method well known to persons skilled in the art. For example, a nucleic acid sequence encoding an amino acid sequence of the designed PPR motif or PPR protein can be determined from the amino acid sequence, and may be cloned to prepare a transformant (such as an expression vector) which produces a desired PPR motif or PPR protein.

Preparation and Use of Fusion Protein:

The present invention relates to a fusion protein of the PPR motif or PPR protein described above (i.e., a polypeptide which can bind RNA base-selectively or RNA base sequence-specifically to the target mRNA) and one or more functional domains which improve a protein expression level from an mRNA.

The "functional domain which improves a protein expression level from an mRNA" which can be used in the present invention may be all or functional part of a functional domain of a known protein which directly or indirectly promotes the translation of the mRNA, for example. More specifically, the functional domain which can be used in the present invention may be a domain which guides ribosome to the mRNA, a domain associated with initiation or promotion of translation of the mRNA, a domain associated with nuclear export of the mRNA, a domain associated with binding to an endoplasmic reticulum membrane, a domain containing an endoplasmic reticulum retention signal (ER retention signal) sequence, or a domain containing an endoplasmic reticulum signal sequence, for example.

More specifically, the domain which guides ribosome to the mRNA may be a domain containing all or functional part of a polypeptide selected from the group consisting of DENR (Density-regulated protein), MCT-1 (Malignant T-cell amplified sequence 1), TPT1 (Translationally-controlled tumor protein), and Lerepo4 (Zinc finger CCCH-domain). The domain associated with initiation or promotion of translation of the mRNA may be a domain containing all or functional part of a polypeptide selected from the group consisting of eIF4E and eIF4G. The domain associated with nuclear export of the mRNA may be a domain containing all or functional part of SLBP (Stem-loop binding protein). The domain associated with binding to an endoplasmic reticulum membrane may be a domain containing all or functional part of a polypeptide selected from the group consisting of SEC61B, TRAP-alpha (Translocon associated protein alpha), SR-alpha, Dial (Cytochrome b5 reductase 3), and p180. The endoplasmic reticulum retention signal (ER retention signal) sequence may be a signal sequence containing a KDEL (KEEL) sequence. The endoplasmic reticulum signal sequence may be a signal sequence containing MGWSCIILFLVATATGAHS (SEQ ID NO: 22).

In the fusion protein according to the present invention, the functional domain may be fused to the N-terminal side of the PPR protein, may be fused to the C-terminal side of the PPR protein, or may be fused to both of the N-terminal side and the C-terminal side thereof. Moreover, the fusion protein according to the present invention may include several functional domains (for example, 2 to 5 functional domains). Furthermore, in the fusion protein according to the present invention, the functional domain and the PPR protein may be indirectly fused via a linker, for example.

The present invention also relates to a nucleic acid encoding the fusion protein described above, and a vector (such as an expression vector) comprising the nucleic acid. The expression vector herein refers to, for example, a vector comprising a DNA having a promoter sequence, a DNA encoding a desired protein, and a DNA having a terminator sequence, in this order from upstream. The expression vector may not have these DNAs in this order as long as it demonstrates desired functions. A variety of expression vectors which can be usually used by persons skilled in the art can be used in the present invention.

Because the fusion protein according to the present invention uses the RNA translation mechanism of eukaryotes, it can function in cells of eukaryotes (such as animals, plants, microorganisms (e.g., yeasts), and protists). The fusion protein according to the present invention can function within animal cells (in vitro or in vivo) in particular. Examples of animal cells into which the fusion protein according to the present invention or a vector which expresses the fusion protein according to the present invention can be introduced can include cells derived from human, monkey, pig, cow, horse, dog, cat, mouse, and rat. Examples of cultured cells into which the fusion protein according to the present invention or a vector which expresses the fusion protein according to the present invention can be introduced can include, but should not be limited to, Chinese hamster ovarian (CHO) cells, COS-1 cells, COS-7 cells, VERO (ATCC CCL-81) cells, BHK cells, dog kidney-derived MDCK cells, hamster AV-12-664 cells, HeLa cells, WI38 cells, 293 cells, 293T cells, and PER.C6 cells.

The terms used herein excluding those particularly defined are used for illustration of the specific embodiments, and are not intended to be limitative to the invention.

The term "comprise" used herein, unless contexts clearly require different understandings, is intended to express that a described entry (such as a member, a step, a component, or a number) is present, and is intended not to exclude the presence of other entries (such as a member, a step, a component, or a number).

Unless otherwise defined, all the terms used herein (including technical terms and scientific terms) have the same meanings as those broadly understood by persons skilled in the art to which the present invention belongs. Unless otherwise clearly defined, the terms used herein should be interpreted as having the meanings consistent to those herein and its related technical field, and should not be interpreted as idealized or excessively formal meanings.

Hereinafter, the present invention will be described more in detail with reference to Examples. However, the present invention can be implemented with a variety of aspects, and should not be construed as limitative to Examples described below.

EXAMPLES

Example 1: Improvement in Protein Expression Level from Target mRNA by Fusion Protein of PPR Motif and eIF4G Materials
(Equipment)
 Basic facility for molecular biological experiment (for construction of plasmids, for example)
 Inverted microscope (DM IL S40, Leica Microsystems, Wetzlar, Germany)
 $CO_2$ incubator (KM-CC17RH2, Panasonic Healthcare, Tokyo, Japan)
 Clean bench (MHE-S1300A2, Panasonic Healthcare, Tokyo, Japan)
 Aspirator (SP-30, Air Liquide Medical Systems, Bovezzo BS, Italy)
 Centrifuge (swing rotor) (LC-200, Tomy Seiko, Tokyo, Japan)
 Ultra-low temperature freezer (−80° C.) (MDF-C8V, Panasonic Healthcare, Tokyo, Japan)
 plate reader (EnSight Kaleido, PerkinElmer, Waltham, Mass., USA)
(Cell Culturing)
 HEK293T cell line (see note 1)

Dulbecco's modified Eagle's culture medium (DMEM, glucose-rich) (see note 2)
100× penicillin-streptomycin solution
Fetal bovine serum (FBS) (see note 3)
EDTA-NaCl solution: 10 mM EDTA and 0.85% (w/v) NaCl, pH adjusted to 7.2 to 7.4, autoclave sterilized, stored at room temperature
100×20 mm cell culture petri dish (Greiner bio one, Frickenhausen, Germany)
10 mL disposable sterilized pipette
15 mL and 50 mL plastic centrifuge tubes
1.8 mL cryotube (Nunc; Thermo Fisher Scientific, Waltham, Mass., USA)
Freeze container (Nalgene; Thermo Fisher Scientific, Waltham, Mass., USA)
Bambanker (Lymphotec, Tokyo, Japan)

(Transfection)
Effector plasmid: pcDNA3.1 (Thermo Fisher Scientific, Waltham, Mass., USA) was used as a basic vector. A fusion gene of PPR and eIF4G is inserted into an expression cassette (100 ng/μL) (see note 4).
Reporter plasmid: pcDNA3.1 (Thermo Fisher Scientific, Waltham, Mass., USA) was used as a basic vector. Luciferase genes are inserted into an expression cassette, and a PPR-binding sequence is inserted into its 5'-UTR (100 ng/μL).
96-well plate coated with poly-L-lysine (AGC Techno glass, Shizuoka, Japan)
1× phosphate-buffered saline, PBS(−): 1.47 mM KHPO$_4$, 8.1 mM Na$_2$HPO$_4$, 137 mM NaCl, and 2.7 mM KCl. pH adjusted to 7.4, autoclave sterilized, stored at room temperature
Hemocytometer (for counting the number of cells) (Improved Neubauer Type Cell counter plate, Watson, Hyogo, Japan)
Transfection reagent (HilyMax, Dojindo Molecular Technologies, Kumamoto, Japan)

(Luciferase Assay)
Dual-Glo Luciferase Assay System (Promega, Madison, Wis., USA.)
96-well luminometer plate (PerkinElmer, Waltham, Mass., USA).

EXPERIMENTAL METHOD (Construction of Vector)
The reporter assay requires an effector plasmid and a reporter plasmid. These two plasmids both are constructed based on pcDNA3.1. The effector plasmid includes a fusion gene encoding a PPR protein and a partial domain of human eIF4G (SEQ ID NO: 1) (FIG. 1A). The PPR protein moiety used was CRR4 (SEQ ID NO: 2). The reporter plasmid includes two open reading frames (ORFs), specifically, renilla luciferase (RLuc) and firefly luciferase (FLuc), which are dicistronically transcribed (FIG. 1A). The RLuc gene is located on the side of the 5'-end of the FLuc gene, and was used as a control of gene expression. The PPR-binding region is inserted into the 5'-UTR of the ORF of FLuc, and consists of three repetitions of a CRR4-recognizing sequence (5'-UAUCUUGUCUUUA-3') (SEQ ID NO: 3) interrupted with four-base sequences (ATCG and GATC). To express both of the fused effector gene and the reporter gene, a cytomegalovirus promoter (CMV) and a bovine growth hormone gene-derived polyadenylation signal were used. For a control experiment, an effector plasmid having no eIF4G was constructed by fusing a FLAG epitope tag to the PPR. A control reporter plasmid without a PPR-binding region was also constructed.

The outline of the procedures from cell culturing to the reporter assay in Examples is shown in FIG. 2.

(Cell Culturing from Frozen Stock)
This step is aseptically performed. All the tools are preliminarily antisepticized with 70% ethanol.
1. A 9 mL DMEM culture medium is placed into a 15 mL centrifuge tube (sterilized).
2. 1 mL of frozen HEK293T cells in a cryotube is incubated within a water bath at 37° C. to quickly melt the cells.
3. The cells are placed into the 15 mL centrifuge tube containing 9 mL DMEM.
4. The centrifuge tube is centrifuged at room temperature and 1100×g for two minutes, and the supernatant is removed.
5. The cells are resuspended in 10 mL DMEM (FBS is added such that the final concentration is 10%).
6. The suspended cells are transferred into a 100 mm petri dish. The petri dish was left to stand in an incubator at 37° C. and under a 5% CO$_2$ condition. If the culturing was started from the frozen stock, the cultured cells were subcultured after 24 hours.

To keep the cells healthy (see note 5), the cell density on the surface of the petri dish is maintained between 10% and 80%. The passage is basically performed every three days (two times a week), or is performed according to the growth rate of the cells. Furthermore, to keep the number of passages small, cells are freshly cultured from the frozen stock once a month. Keeping the number of passages small and thus keeping the cells healthy are important for efficient DNA transfection.

(Passages to Maintain Cells)
1. New 100 mm petri dishes are provided as required. 8 mL DMEM and 1 mL FBS are preliminarily placed onto each of the petri dishes.
2. The culture medium on a petri dish containing the cultured cells is removed with an aspirator (see note 6).
3. 2 mL EDTA-NaCl solution is gently added onto adhering cells on the surface of the petri dish so as not to peel off the cells. The petri dish is turned around to evenly distribute the solution across the entire surface of the petri dish. The EDTA-NaCl solution is removed with an aspirator. The petri dish is tapped to peel off the cells.
4. 10 mL DMEM is added to the cells in the petri dish, and the cells are suspended by gently pipetting.
5. 1 mL suspended cells (10W cultured cells) are added to the petri dishes preliminarily provided and each containing 9 mL culture medium. Each of the petri dishes is turned around to distribute the cells across the entire surface thereof.

(Freeze Storage of Cells)
A frozen stock is prepared with Bambanker reagent and cultured cells in a logarithmic growth phase at a cell density up to 50W. Use of Bambanker provides a high recovery rate and facilitates long-term storage.
1. The cells on the second day since the passage are peeled off according to the procedure for passage. 5 to 10 mL DMEM is added, and the cells are recovered in a 50 mL centrifuge tube.
2. The centrifuge tube is centrifuged at room temperature and 1100×g for two minutes, and the supernatant is removed.
3. 1 mL Bambanker per petri dish is added to suspend the cells.

4. The suspended cells are quickly dispensed into cryotubes, and the cryotubes are covered with their lids.

5. The cryotubes are placed in a dedicated freeze container, and are left to stand at −80° C. for 12 hours (see note 7).

6. The cryotubes are transferred into a standard sample box, and are stored at −80° C. or in liquid nitrogen.

(Transient Gene Introduction (Transfection))

1. Before starting transfection, petri dishes each containing the cells on the second day since the passage are provided as required, and the cells are checked whether they are healthy (normal) or not (see note 8). About 96 assays can be performed with one petri dish as an estimate.

2. The cells on the second day since the passage are peeled off according to the procedure for passage, and the suspended cells are transferred into a 50 mL centrifuge tube.

3. The centrifuge tube is centrifuged at room temperature and 1100×g for two minutes, and the supernatant is removed.

4. Cell clusters are completely dispersed in 10 mL DMEM (FBS is added such that the final concentration is 10%).

5. The number of cells is counted with a hemocytometer and an inverted microscope. The cells are suspended in an appropriate amount of DMEM (FBS is added such that the final concentration is 10%) such that the number of cells is 1 to $2\times10^5$ cells/mL.

6. A 96-well plate is provided. 200 μL (2 to $4\times10^4$ cells/mL) per well of suspended cultured cells is placed into each well, and the plate is left to stand overnight in an incubator at 37° C. under a 5% $CO_2$ condition. One well is used for one assay.

7. On the next day, the culture medium is carefully removed from each well, and is replaced with 100 μL of new DMEM (FBS is added such that the final concentration is 10%).

8. 400 ng effector plasmid (4 μL of 100 ng/μL) and 100 ng reporter plasmid (1 μL of 100 ng/μL) are placed into a single well on a new 96-well PCR plate (or a 0.2 mL tube).

9. For one assay, 1 μL HilyMAX is diluted with 10 μL serum-free DMEM.

10. 11 μL diluted solution is placed into each of the wells containing the plasmids. The solution is well mixed with the plasmids by pipetting.

11. The solution is left to stand at room temperature for 15 minutes. The total amount of the mixture is placed into the wells containing the cultured cells. The plate is left to stand in an incubator at 37° C. under a 5% $CO_2$ condition for 24 hours.

(Luciferase Assay)

The dual luciferase assay is performed using Dual-Glo Luciferase Assay System according to the usage instruction from the manufacturer except for a few modifications.

1. After 24 hours from the transfection, the culture medium of each well is replaced with 40 μL 1×PBS(−).

2. 40 μL of Dual-Glo luciferase reagent is placed into each well, and is well mixed with the culture medium by pipetting.

3. The mixture is left to stand at room temperature for 10 minutes, and the total amount thereof is transferred into a 96-well luminometer plate.

4. The light emission from firefly luciferase related with expression of FLuc gene is measured with a plate reader.

5. A Stop & Glo substrate is 100-fold diluted with a Dual-Glo Stop & Glo buffer. 40 μL of the diluted solution is added into each well.

6. The plate is left to stand at least at room temperature for 10 minutes, and then the light emission from renilla luciferase related with expression of RLuc gene is measured.

(Data Analysis)

1. The value of FLuc/RLuc is calculated to correct a difference in transfection efficiency between the assays or experimental errors.

2. An increase in activity of reporter gene expression is determined in the presence of the PPR-binding region and in the absence thereof by dividing an experimental value obtained using the plasmid according to the present invention (plasmid encoding a fusion protein of CRR4 and a translation activation domain eIF4G) by an experimental value obtained using a control plasmid (plasmid encoding a fusion protein of CRR4 and FLAG-tag).

EXPERIMENTAL RESULTS

The results of the luciferase assay are shown in FIG. 3. As shown in FIG. 3, 2.75-fold translation activity was specifically verified in the presence of both of the PPR-eIF4G and the PPR-binding sequence. That is, it is demonstrated that the fusion protein of the PPR protein and the functional domain which improve a protein expression level from an mRNA improves the protein expression level from the target mRNA.

Notes (Note 1) HEK293T is a human fetus-derived kidney cell line which expresses an SV40 large T antigen. The cell line is readily cultured, and can be transfected with high efficiency by a variety of methods. HEK293T cells are available from RIKEN BRC (ja.brc.riken.jp) or ATCC (www.atcc.org).

(Note 2) 1× penicillin-streptomycin solution is added to DMEM to avoid contamination with microorganisms.

(Note 3) Before use, FBS is inactivated at 56° C. for 30 minutes, and is stored at 4° C.

(Note 4) The purity of the plasmid is significantly important to the transfection efficiency. The plasmid should be isolated using a kit of a transfection grade.

(Note 5) A daily growth rate is an index indicating that the cells are healthy. To avoid suppression of cell growth, the cells should be always cultured in a sufficient space under a sufficient nutritional condition.

(Note 6) HEK293T cells should be gently treated when the culture medium is replaced because the cells are readily peeled off from the culturing petri dish.

(Note 7) The dedicated freeze container is a box whose freezing speed can be adjusted (about −1° C. per minute at −80° C.), and enables the cells to be freeze stored in a non-programmable −80° C. freezer.

(Note 8) In transfection, cells are used at a culture density of 50 to 80%. However, an appropriate cell density depends on the transfection reagent. Additionally, the ratio of the transfection reagent (μL) to the plasmid DNA (pg) should be also optimized according to the usage instructions from the manufacturer. The procedure described herein is optimized for a condition where a 96-well plate, HEK293T cells, and HilyMAX as a transfection reagent are used.

Example 2: Improvement in Protein Expression Level from Target mRNA by Fusion Protein of PPR and Another Functional Domain In the case where useful substances are produced using cells, the amounts of protein synthesized by endogenous genes and exogenous genes should be precisely controlled.

The final amount of the synthesized protein is determined by the insertion positions of genes, the mRNA transcription amount, post-transcriptional regulation (regulation at an RNA level), post-translational modification, and the like. For these reasons, the present inventors have devised a method of enhancing the translation of mRNAs taking advantage of the fact that a PPR protein sequence-specifically binds to a target RNA molecule (FIG. 4). In the translation of mRNAs in eukaryotes, an mRNA undergoes action of a translation initiation factor (eukaryotic initiation factor; eIF). As a result, the ribosome is recruited near the translation starting point, and then the translation of the mRNA is started. In other words, the present inventors have considered that the translation of the mRNA can be artificially enhanced if the ribosome can only be recruited onto the mRNA. Moreover, the translation of an mRNA into a protein is usually performed in the ER. For this reason, the present inventors have considered that the translation of the mRNA can be enhanced by intentionally localizing the target mRNA into the ER.

Verification by Experiment

To verify the idea above, a reporter assay system using animal cultured cells (HEK293T) was prepared (the experiment was performed by the same method as that in Example 1 except that different functional domains were used). The system was constructed using CRR4 protein (one of *Arabidopsis thaliana* PPR proteins), which is known to bind to a specific RNA sequence (UAUCUUGUCUUUA) (SEQ ID NO: 3). First, a fusion protein expression vector (effector plasmid) of CRR4 and a candidate protein functional domain was prepared. The selected candidate domains were (a) eIF proteins (eIF4E and eIF4G), (b) ribosome-bound proteins (DENR, MCT-1, TPT1, and Lerepo4), (c) translational regulation factors (SLBPs) of Histone which promote transport of the transcribed mRNA from the nucleus to the cytoplasm, (d) ER anchor proteins (SEC61B, TRAP-alpha, SR-alpha, Dial, and p180), (e) ER retention signal (KDEL), and (f) ER signal peptide. The fusion proteins were cloned so as to express in the form of HA-CRR4-XX or XX-CRR4-HA (HA: epitope tag (SEQ ID NO: 4); XX: candidate domain).

The reporter plasmid included an expression cassette where renilla luciferase (RLuc) and firefly luciferase (FLuc) are transcribed in the form of a dicistronic mRNA under the control of a CMV promoter. Three PPR-binding sequences (UAUCUUGUCUUUA) (SEQ ID NO: 3) are inserted into a site on the 5'-end of Fluc.

The effector plasmid and the reporter plasmid were transfected into HEK293T cells, and the intensities of light emission from RLUC and FLUC were measured. The intensity of light emission from RLUC was treated as a transfection control, and the value of the intensity of light emission from FLUC/the intensity of light emission from RLUC was treated as a translation activity amount.

Results

The results shown in FIGS. 5 and 6 were examined using the following indices (A) and (B).
(A) Comparison between the absence of and the presence of the target
The comparison shows an amount of sequence-specific change in translation.
(B) Comparison to the presence of the target and the absence of the effector (empty) (black dashed line)
The comparison shows an amount of change in translation caused by addition of the domain.
1. eIF4E was fused to the C-terminal side of CRR4.
(A) 2.7 times
(B) 1.6 times
2. eIF4G was fused to the C-terminal side of CRR4.
(A) 4.5 times
(B) 3.3 times
3. DENR was fused to the N-terminal side of CRR4.
(A) 1.7 times
(B) 1.3 times
4. DENR was fused to the C-terminal side of CRR4.
(A) 2.4 times
(B) 1.7 times
5. MCT-1 was fused to the N-terminal side of CRR4.
(A) 1.3 times
(B) 1.0 time
6. MCT-1 was fused to the C-terminal side of CRR4.
(A) 2.0 times
(B) 1.2 times
7. TPT-1 was fused to the N-terminal side of CRR4.
(A) 1.4 times
(B) 1.0 time
8. TPT-1 was fused to the C-terminal side of CRR4.
(A) 2.4 times
(B) 1.9 times
9. Lerepo4 was fused to the N-terminal side of CRR4.
(A) 3.0 times
(B) 1.8 times
10. Lerepo4 was fused to the C-terminal side of CRR4.
(A) 3.3 times
(B) 2.6 times
11. SLBP was fused to the C-terminal side of CRR4.
(A) 4.1 times
(B) 3.3 times
12. Sec61B was fused to the C-terminal side of CRR4.
(A) 1.6 times
(B) 1.6 times
13. Sec61BTM was fused to the C-terminal side of CRR4.
(A) 2.4 times
(B) 1.9 times
14. TRAP-alpha was fused to the C-terminal side of CRR4.
(A) 3.5 times
(B) 4.5 times
15. TRAPTM was fused to the C-terminal side of CRR4.
(A) 2.3 times
(B) 1.6 times
16. SR-alpha was fused to the N-terminal side of CRR4.
(A) 1.7 times
(B) 1.5 times
17. DialTM was fused to the N-terminal side of CRR4.
(A) 1.8 times
(B) 1.2 times
18. P180TM2R was fused to the N-terminal side of CRR4.
(A) 2.1 times
(B) 1.5 times
19. P180TMH was fused to the N-terminal side of CRR4.
(A) 2.3 times
(B) 2.5 times
20. P180TM2 was fused to the N-terminal side of CRR4.
(A) 3.0 times
(B) 2.1 times
21. KDEL was fused to the C-terminal side of CRR4.
(A) 1.8 times
(B) 1.4 times
22. KEEL was fused to the C-terminal side of CRR4.
(A) 2.3 times
(B) 2.1 times
23. Signal peptide (SP) was fused to the N-terminal side of CRR4.
(A) 1.4 times (B) 2.0 times As shown above, an increase in translation was found in all the functional domains in both of the indices (A) and the targets (B). Namely, it was clearly shown that the fusion protein according to the present invention can enhance the translation of the target mRNA.

The amino acid sequences of the functional domains used in Examples are listed below in Table 1.

TABLE 1

| Domain | Sequence |
|---|---|
| eIF4E | MATVEPETTPTPNPPTTEEEKTESNQEVANPEHYIKHPLQNRWALW FFKNDKSKTWQANLRLISKFDTVEDFWALYNHIQLSSNLMPGCDYS LFKDGIEPMLEDEKNKRGGRWLITLNKQQRRSDLDRFWLETLLCLI GESFDDYSDDVCGAVVNVRAKGDKIAIWTTECENREAVTHIGRVYK ERLGLPPKIVIGYQSHADTATKSGSTTKNRFVVGRY (SEQ ID NO: 5) |
| eIF4G | EEKKRYDREFLLGFQFIFASMQKPEGLPHISDVVLDKANKTPLRPL DPTRLQGINCGPDFTPSFANLGRTTLSTRGPPRGGPGGELPRGPQA GLGPRRSQQGPRKEPRKIIATVLMTEDIKLNKAEKAWKPSSKRTAA DKDRGEEDADGSKTQDLFRRVRSILNKLTPQMFQQLMKQVTQLAID TEERLKGVIDLIFEKAISEPNFSVAYANMCRCLMALKVPTTEKPTV TVNFRKLLLNRCQKEFEKDKDDDEVFEKKQKEMDEAATAEEERGRLK EELEEARDIARRRSLGNIKFIGELFKLKMLTEAIMHDCVVKLLKNH DEESLECLCRLLTTIGKDLDFEKAKPRMDQYFNQMEKIIKEKKTSS RIRFMLQDVLDLRGSNWVPRRGDQGPKTIDQIHKEAEMEEHREHIK VQQLMAKGSDKRRGGPPGPPISRGLPLVDDGGWNTVPISKGSRPID TSRLTKITKPGSIDSNNQLFAPGGRLSWGKGSSGGSGAKPSDAASE AARPATSTLNRFSALQQAVPTESTDNRRVVQRSSLSRERGEKAGDR GDRLERSERGGDRGDRLDRARTPATKRSFSKEVEERSRERPSQPEG LRKAASLTEDRDRGRDAVKREAALPPVSPLKAALSEEELEKKSKAI IEEYLHLNDMKEAVQCVQELASPSLLFIFVRHGVESTLERSAIARE HMGQLLHQLLCAGHLSTAQYYQGLYEILELAEDMEIDIPHVWLYLA ELVTPILQEGGVPMGELFREITKPLRPLGKAASLLLEILGLLCKSM GPKKVGTLWREAGLSWKEFLPEGQDIGAFVAEQKVEYTLGEESEAP GQRALPSEELNRQLEKLLKEGSSNQRVFDWIEANLSEQQIVSNTLV RALMTAVCYSAIIFETPLRVDVAVLKARAKLLQKYLCDEQKELQAL YALQALVVTLEQPPNLLRMFFDALYDEDVVKEDAFYSWESSKDPAE QQGKGVALKSVTAFFKWLREAEEESDH (SEQ ID NO: 1) |
| DENR | MAADISESSGADCKGDPRNSAKLDADYPLRVLYCGVCSLPTEYCEY MPDVAKCRQWLEKNFPNEFAKLTVENSPKQEAGISEGQGTAGEEEE KKKQKRGGRGQIKQRKKTVPQKVTIAKIPRAKKKYVTRVCGLATFF IDLKEAQRFFAQKFSCGASVTGEDEIIIQGDFTDDIIDVIQEKWPE VDDDSIEDLGEVKK (SEQ ID NO: 6) |
| MCT-1 | MFKKFDEKENVSNCIQLKTSVIKGIKNQLIEQFPGIEPWLNQIMPK KDPVKIVRCHEHIEILTVNGELLFFRQREGPFYPTLRLLHKYPFIL PHQQVDKGAIKFVLSGANIMCPGLTSPGAKLYPAAVDTIVAIMAEG KQHALCVGVMKMSAEDIEKVNKGIGIENIHYLNDGLWHMKTYK (SEQ ID NO: 7) |
| TPT-1 | MIIYRDLISHDEMFSDIYKIREIADGLCLEVEGKMVSRTEGNIDDS LIGGNASAEGPEGEGTESTVITGVDIVMNHHLQETSFTKEAYKKYI KDYMKSIKGKLEEQRPERVKPFMTGAAEQIKHILANFKNYQFFIGE NMNPDGMVALLDYREDGVTPYMIFFKDGLEMEKC (SEQ ID NO: 8) |
| Lerepo4 | PPKKQAQAGGSKKAEQKKKEKIIEDKTFGLKNKKGAKQQKFIKAVT HQVKFGQQNPRQVAQSEAEKKLKKDDKKKELQELNELFKPVVAAQK ISKGADPKSVVCAFFKQGQCTKGDKCKFSHDLTLERKCEKRSVYID ARDEELEKDTMDNWDEKKLEEVVNKKHGEAEKKKPKTQIVCKHFLE AIENNKYGWFWVCPGGGDICMYRHALPPGFVLKKDKKKEEKEDEIS LEDLIERERSALGPNVTKITLESFLAWKKRKRQEKIDKLEQDMERR KADFKAGKALVISGREVFEFRPELVNDDDEEADDTRYTQGTGGDEV DDSVSVNDIDLSLYIPRDVDETGITVASLERFSTYTSDKDENKLSE ASGGRAENGERSDLEEDNEREGTENGAIDAVPVDEKSFHWRGFG (SEQ ID NO: 9) |
| SLBP | ACRPRSPPRHQSRCDGDASPPSPARWSLGRKRRADGRRWRPEDAEE AEHRGAERRPESFTTPEGPKPRSRCSDWASAVEEDEMRTRVNKEMA RYKRKLLINDFGRERKSSSGSSDSKESMSTVPADFETDESVLMRRQ KQINYGKNTIAYDRYIKEVPRHLRQPGIHPKTPNKFKKYSRRSWDQ QIKLWKVALHFWDPPAEEGCDLQEIHPVDLESAESSSEPQTSSQDD FDVYSGTPTKVRHMDSQVEDEFDLEACLTEPLRDFSAMS (SEQ ID NO: 10) |
| Sec61B | PGPTPSGTNVGSSGRSPSKAVAARAAGSTVRQRKNASCGTRSAGRT TSAGTGGMWRFYTEDSPGLKVGPVPVLVMSLLFIASVFMLHIWGKY TRS (SEQ ID NO: 11) |
| Sec61B-TM | VGPVPVLVMSLLFIASVFMLHIW (SEQ ID NO: 12) |

TABLE 1-continued

| Domain | Sequence |
|---|---|
| TRAP-alpha | RLLPRLLLLLLLVFPATVLFRGGPRGLLAVAQDLTEDEETVEDSII EDEDDEAEVEEDEPTDLVEDKEEEDVSGEPEASPSADTTILFVKGE DFPANNIVKFLVGFTNKGTEDFIVESLDASFRYPQDYQFYIQNFTA LPLNTVVPPQRQATFEYSFIPAEPMGGRPFGLVINLNYKDLNGNVF QDAVFNQTVTVIEREDGLDGETIFMYMFLAGLGLLVIVGLHQLLES RKRKRPIQKVEMGTSSQNDVDMSWIPQETLNQINKASPRRLPRKRA QKRSVGSDE (SEQ ID NO: 13) |
| TRAP-TM | TIFMYMFLAGLGLLVIVGLHQLL (SEQ ID NO: 14) |
| SR-alpha | LDFFTIFSKGGLVLWCFQGVSDSCTGPVNALIRSVLLQVGFQKILT LTYVDKLIDDVHRLFRDKYRTEIQQQSALSLLNGTFDFQNDFLRLL REAEESSKIRAPTTMKKFEDSEKAKKPVRSMIETRGEKPKEKAKNS KKKGAKKEGSDGPLATSKPVPAEKSGLPVGPENGVELSKEELIRRK REEFIQKHGRGMEKSNKSTKSDAPKEKGKKAPRVWELGGCANKEVL DYSTPTTNGTPEAALSEDINLIRGTGSGGQLQDLDCSSSDDEGAAQ NSTKPSATKGTLGGMFGMLKGLVGSKSLSREDMESVLDKMRDHLIA KNVAADIAVQLCESVANKLEGKVMGTFSTVTSTVKQALQESLVQIL QPQRRVDMLRDIMDAQRRQRPYVVTFCGVNGVGKSTNLAKISFWLL ENGFSVLIAACDTFRAGAVEQLRTHTRRLSALHPPEKHGGRTMVQL FEKGYGKDAAGIAMEAIAFARNQGFDVVLVDTAGRMQDNAPLMTAL AKLITVNTPDLVLFVGEALVGNEAVDQLVKFNRALADHSMAQTPRL IDGIVLTKFDTIDDKVGAAISMTYITSKPIVFVGTGQTYCDLRSLN AKAVVAALMKA (SEQ ID NO: 15) |
| DiaTM | STLGHMVLFPVWFLYSLL (SEQ ID NO: 16) |
| P180TMR2 | DIYDTQTLGVVVFGGFMVVSAIGIFLVSTFSMKETSYEEALANQRK EMAKTHHQKVEKKKKEKTVEKKGKTKKKEEKPNGKIPDHDPAPNVT VLLREPVRAPAVAVAPTPVQPPIIVAPVATVPAMPQEKLASSPKDK KKKEKKVAKVEPAVSSVVNSIQVLTSKAAILETAPKEGRNTDVAQS PEAPKQEAPAKKKSGSKKKGPPDADGPLYLPYKTLVSTVGSMVFNE GEAQRLIEILSEKAGIIQDTWHKATQKGDPV (SEQ ID NO: 17) |
| P180TMH | LGVVVFGGFMVVSAIGIFLVSTF (SEQ ID NO: 18) |
| P180TM2 | DIYDTQTLGVVVFGGFMVVSAIGIFLVSTF (SEQ ID NO: 19) |
| KDEL | KDEL (SEQ ID NO: 20) |
| KEEL | KEEL (SEQ ID NO: 21) |
| ER signal peptide | MGWSCIILFLVATATGAHS (SEQ ID NO: 22) |

The invention claimed is:

1. A fusion protein for improving a protein expression level from a target mRNA, the fusion protein comprising:
   (A) one or more functional domains which improve a protein expression level from an mRNA; and
   (B) a polypeptide moiety which can bind to a target mRNA in an RNA base-selective or RNA base sequence-specific manner,
   wherein the polypeptide moiety of (B) comprises one or more PPR motifs, each PPR motif comprising a polypeptide consisting of 30 to 38 amino acids in length and being represented by Formula 1:

(Helix A)-X-(Helix B)-L        (Formula 1)

where Helix A is a moiety which consists of 12 amino acids in length and can form an α-helix structure, and is represented by Formula 2:

$A_1$-$A_2$-$A_3$-$A_4$-$A_5$-$A_6$-$A_7$-$A_8$-$A_9$-$A_{10}$-$A_{11}$-$A_{12}$        (Formula 2)

where $A_1$ to $A_{12}$ each independently represent an amino acid;

X is not present, or is a moiety consisting of 1 to 9 amino acids in length;

Helix B is a moiety which consists of 11 to 13 amino acids in length and can form an α-helix structure;

L is a moiety consisting of 2 to 7 amino acids in length and represented by Formula 3:

   (Formula 3)

where the amino acids are numbered from the C-terminal as "i" (−1), "ii" (−2), ... and $L_{iii}$ to $L_{vii}$ may not be present, and a combination of three amino acids $A_1$, $A_4$, and $L_{ii}$ or a combination of two amino acids $A_4$ and $L_{ii}$ corresponds to a base or base sequence of the target mRNA, wherein the one or more functional domains (A) are selected from the group consisting of a domain which guides ribosome to the mRNA, a domain which initiates or promotes translation of the mRNA, a domain associated with nuclear export of the mRNA, a domain which binds to an endoplasmic reticulum membrane, a domain containing an endoplasmic reticulum retention signal (ER retention signal) sequence, and a domain containing an endoplasmic reticulum signal sequence.

2. The fusion protein according to claim 1, wherein the polypeptide moiety of (B) comprises a plurality of 2 to 30 PPR motifs, and the plurality of PPR motifs is arranged so as to specifically bind to the base sequence of the target mRNA.

3. The fusion protein according to claim 2, wherein the polypeptide moiety of (B) comprises a plurality of 5 to 25 PPR motifs.

4. The fusion protein according to claim 1, wherein one or more functional domains of (A) each bind to an N-terminal and/or a C-terminal of the polypeptide moiety of (B).

5. The fusion protein according to claim 1, wherein the domain which guides ribosome to the mRNA is a domain containing all or a functional part of a polypeptide selected from the group consisting of DENR (Density-regulated protein), MCT-1 (Malignant T-cell amplified sequence 1), TPT1 (Translationally-controlled tumor protein), and Lerepo4 (Zinc finger CCCH-domain), the domain which initiates or promotes translation of the mRNA is a domain containing all or a functional part of a polypeptide selected from the group consisting of eIF4E and eIF4G, the domain associated with nuclear export of the mRNA is a domain containing all or a functional part of SLBP (Stem-loop binding protein), the domain which binds to an endoplasmic reticulum membrane is a domain containing all or a functional part of a polypeptide selected from the group consisting of SEC61B, TRAP-alpha (Translocon associated protein alpha), SR-alpha, Dial (Cytochrome b5 reductase 3), and p180, the endoplasmic reticulum retention signal (ER retention signal) sequence is a signal sequence containing a KDEL (SEQ ID NO:20) or (KEEL) (SEQ ID NO:21) sequence, and/or the endoplasmic reticulum signal sequence is a signal sequence containing (SEQ ID NO: 22)
MGWSCIILFLVATATGAHS.

6. The fusion protein according to claim 1, wherein the combination of the three amino acids $A_1$, $A_4$, and $L_{ii}$ in each of the PPR motifs is:

(valine, threonine, asparagine), (phenylalanine, serine, asparagine), (phenylalanine, threonine, asparagine), (isoleucine, asparagine, aspartic acid), or (threonine, threonine, asparagine) in order of ($A_1$, $A_4$, $L_{ii}$) when a target base for the PPR motif is A (adenine);

(glutamic acid, glycine, aspartic acid), (valine, threonine, aspartic acid), (lysine, threonine, aspartic acid), or (leucine, threonine, aspartic acid) in order of ($A_1$, $A_4$, $L_{ii}$) when the target base for the PPR motif is G (guanine);

(valine, asparagine, aspartic acid), (isoleucine, asparagine, asparagine), (isoleucine, asparagine, aspartic acid), (isoleucine, methionine, aspartic acid), (phenylalanine, proline, aspartic acid), or (tyrosine, proline, aspartic acid) in order of ($A_1$, $A_4$, $L_{ii}$) when the target base for the PPR motif is U (uracil); or (valine, asparagine, asparagine), (isoleucine, asparagine, asparagine), (valine, asparagine, serine), or (isoleucine, methionine, aspartic acid) in order of ($A_1$, $A_4$, $L_{ii}$) when the target base for the PPR motif is C (cytosine).

7. The fusion protein according to claim 1, wherein the combination of the two amino acids $A_4$ and $L_{ii}$ in each of the PPR motifs is:

(threonine, asparagine), (serine, asparagine), or (glycine, asparagine) in order of ($A_4$, $L_{ii}$) when a target base for the PPR motif is A (adenine);

(threonine, aspartic acid) or (glycine, aspartic acid) in order of ($A_4$, $L_{ii}$) when the target base for the PPR motif is G (guanine);

(asparagine, aspartic acid), (proline, aspartic acid), (methionine, aspartic acid), or (valine, threonine) in order of ($A_4$, $L_{ii}$) when the target base for the PPR motif is U (uracil); or (asparagine, asparagine), (asparagine, serine), or (leucine, aspartic acid) in order of ($A_4$, $L_{ii}$) when the target base for the PPR motif is C (cytosine).

8. A nucleic acid encoding the fusion protein according to claim 1.

9. A vector comprising the nucleic acid according to claim 8.

10. The vector according to claim 9, wherein the vector is an expression vector.

11. A method of improving a protein expression level from a target mRNA within a cell, the method comprising:
introducing the fusion protein of claim 1 or a nucleic acid encoding the fusion protein into a cell.

12. The method according to claim 11, wherein the cell is a eukaryotic cell.

13. The method according to claim 12, wherein the cell is an animal cell.

14. The method according to claim 13, wherein the animal cell is a human cell.

15. The method of claim 11, wherein the fusion protein is encoded on a vector.

16. The method according to claim 5, wherein the polypeptide moiety (B) comprises a CRR4-binding sequence.

17. The method according to claim 5, wherein the one or more functional domains comprise a domain containing all or a functional part of a polypeptide of SEQ ID NO: 6 (DENR; Density-regulated protein), SEQ ID NO: 7 (MCT-1; Malignant T-cell amplified sequence 1), SEQ ID NO: 8 (TPT1; Translationally-controlled tumor protein), SEQ ID NO: 9 (Lerepo4; Zinc finger CCCH-domain), SEQ ID. NO. 5 (eIF4E), SEQ ID NO: 1 (eIF4G), SEQ ID NO: 10 (SLBP;

Stem-loop binding protein), SEQ ID NO: 11(SEC61B), SEQ ID NO: 13 (TRAP-alpha; Translocon associated protein alpha), SEQ ID NO: 15 (SR-alpha), SEQ ID NO: 16 (Dial; Cytochrome b5 reductase 3), SEQ ID NO: 17 (p180 TMR2), SEQ ID NO: 18 (p180TMH), SEQ ID NO: 19 (p180TM2), SEQ ID NO:20 (KDEL), SEQ ID NO:21 (KEEL), and/or SEQ ID NO:22 (ER signal peptide).

18. The method of claim 17, wherein the polypeptide moiety (B) comprises a CRR4-binding sequence.

19. The method of claim 18, wherein the CRR4-binding sequence is SEQ ID NO. 2.

* * * * *

UNITED STATES PATENT AND TRADEMARK OFFICE
CERTIFICATE OF CORRECTION

| | |
|---|---|
| PATENT NO. | : 11,136,361 B2 |
| APPLICATION NO. | : 16/305080 |
| DATED | : October 5, 2021 |
| INVENTOR(S) | : Nakamura et al. |

It is certified that error appears in the above-identified patent and that said Letters Patent is hereby corrected as shown below:

On the Title Page

(56) References Cited, FOREIGN PATENT DOCUMENTS: Please correct "WO 2011/111828 9/2011" to read -- WO 2011/111829 9/2011 --

In the Specification

Column 3, Line 14: Please correct "Dial" to read -- Dia1 --

Column 9, Line 38: Please correct "Dial" to read -- Dia1 --

Column 11, Line 30: Please correct "KHPO$_4$" to read -- KH$_2$PO$_4$ --

Column 12, Line 49: Please correct "10W" to read -- 10% --

Column 12, Line 57: Please correct "50W" to read -- 50% --

Column 14, Line 55: Please correct "(pg)" to read -- (µg) --

Column 15, Line 37: Please correct "Dial" to read -- Dia1 --

Column 16, Line 47: Please correct "DialTM" to read -- Dia1TM --

Column 19, Table 1, Line 31: Please correct "DiaTM" to read -- Dia1TM --

In the Claims

Column 47, Line 55, Claim 5: Please correct "Dial" to read -- Dia1 --

Column 49, Line 3, Claim 17: Please correct "Dial" to read -- Dia1 --

Signed and Sealed this
Third Day of May, 2022

Katherine Kelly Vidal
*Director of the United States Patent and Trademark Office*

SEQUENCE LISTING

<160> NUMBER OF SEQ ID NOS: 22

<210> SEQ ID NO 1
<211> LENGTH: 993
<212> TYPE: PRT
<213> ORGANISM: Homo sapiens

<400> SEQUENCE: 1

Glu Glu Lys Lys Arg Tyr Asp Arg Glu Phe Leu Leu Gly Phe Gln Phe
1               5                   10                  15

Ile Phe Ala Ser Met Gln Lys Pro Glu Gly Leu Pro His Ile Ser Asp
                20                  25                  30

Val Val Leu Asp Lys Ala Asn Lys Thr Pro Leu Arg Pro Leu Asp Pro
            35                  40                  45

Thr Arg Leu Gln Gly Ile Asn Cys Gly Pro Asp Phe Thr Pro Ser Phe
        50                  55                  60

Ala Asn Leu Gly Arg Thr Thr Leu Ser Thr Arg Gly Pro Pro Arg Gly
65                  70                  75                  80

Gly Pro Gly Gly Glu Leu Pro Arg Gly Pro Gln Ala Gly Leu Gly Pro

-continued

```
                     85                  90                  95
Arg Arg Ser Gln Gln Gly Pro Arg Lys Glu Pro Arg Lys Ile Ile Ala
                100                 105                 110
Thr Val Leu Met Thr Glu Asp Ile Lys Leu Asn Lys Ala Glu Lys Ala
                115                 120                 125
Trp Lys Pro Ser Ser Lys Arg Thr Ala Ala Asp Lys Asp Arg Gly Glu
                130                 135                 140
Glu Asp Ala Asp Gly Ser Lys Thr Gln Asp Leu Phe Arg Arg Val Arg
145                 150                 155                 160
Ser Ile Leu Asn Lys Leu Thr Pro Gln Met Phe Gln Gln Leu Met Lys
                165                 170                 175
Gln Val Thr Gln Leu Ala Ile Asp Thr Glu Arg Leu Lys Gly Val
                180                 185                 190
Ile Asp Leu Ile Phe Glu Lys Ala Ile Ser Glu Pro Asn Phe Ser Val
                195                 200                 205
Ala Tyr Ala Asn Met Cys Arg Cys Leu Met Ala Leu Lys Val Pro Thr
                210                 215                 220
Thr Glu Lys Pro Thr Val Thr Val Asn Phe Arg Lys Leu Leu Leu Asn
225                 230                 235                 240
Arg Cys Gln Lys Glu Phe Glu Lys Asp Lys Asp Asp Glu Val Phe
                245                 250                 255
Glu Lys Lys Gln Lys Glu Met Asp Glu Ala Ala Thr Ala Glu Glu Arg
                260                 265                 270
Gly Arg Leu Lys Glu Glu Leu Glu Ala Arg Asp Ile Ala Arg Arg
                275                 280                 285
Arg Ser Leu Gly Asn Ile Lys Phe Ile Gly Glu Leu Phe Lys Leu Lys
                290                 295                 300
Met Leu Thr Glu Ala Ile Met His Asp Cys Val Val Lys Leu Leu Lys
305                 310                 315                 320
Asn His Asp Glu Glu Ser Leu Glu Cys Leu Cys Arg Leu Leu Thr Thr
                325                 330                 335
Ile Gly Lys Asp Leu Asp Phe Glu Lys Ala Lys Pro Arg Met Asp Gln
                340                 345                 350
Tyr Phe Asn Gln Met Glu Lys Ile Ile Lys Glu Lys Lys Thr Ser Ser
                355                 360                 365
Arg Ile Arg Phe Met Leu Gln Asp Val Leu Asp Leu Arg Gly Ser Asn
                370                 375                 380
Trp Val Pro Arg Arg Gly Asp Gln Gly Pro Lys Thr Ile Asp Gln Ile
385                 390                 395                 400
His Lys Glu Ala Glu Met Glu Glu His Arg Glu His Ile Lys Val Gln
                405                 410                 415
Gln Leu Met Ala Lys Gly Ser Asp Lys Arg Arg Gly Pro Pro Gly
                420                 425                 430
Pro Pro Ile Ser Arg Gly Leu Pro Leu Val Asp Asp Gly Gly Trp Asn
                435                 440                 445
Thr Val Pro Ile Ser Lys Gly Ser Arg Pro Ile Asp Thr Ser Arg Leu
                450                 455                 460
Thr Lys Ile Thr Lys Pro Gly Ser Ile Asp Ser Asn Asn Gln Leu Phe
465                 470                 475                 480
Ala Pro Gly Gly Arg Leu Ser Trp Gly Lys Gly Ser Ser Gly Gly Ser
                485                 490                 495
Gly Ala Lys Pro Ser Asp Ala Ala Ser Glu Ala Ala Arg Pro Ala Thr
                500                 505                 510
```

```
Ser Thr Leu Asn Arg Phe Ser Ala Leu Gln Gln Ala Val Pro Thr Glu
        515                 520                 525

Ser Thr Asp Asn Arg Arg Val Val Gln Arg Ser Ser Leu Ser Arg Glu
530                 535                 540

Arg Gly Glu Lys Ala Gly Asp Arg Gly Asp Arg Leu Glu Arg Ser Glu
545                 550                 555                 560

Arg Gly Gly Asp Arg Gly Asp Arg Leu Asp Arg Ala Arg Thr Pro Ala
                565                 570                 575

Thr Lys Arg Ser Phe Ser Lys Glu Val Glu Arg Ser Arg Glu Arg
                580                 585                 590

Pro Ser Gln Pro Glu Gly Leu Arg Lys Ala Ala Ser Leu Thr Glu Asp
        595                 600                 605

Arg Asp Arg Gly Arg Asp Ala Val Lys Arg Glu Ala Ala Leu Pro Pro
        610                 615                 620

Val Ser Pro Leu Lys Ala Ala Leu Ser Glu Glu Leu Glu Lys Lys
625                 630                 635                 640

Ser Lys Ala Ile Ile Glu Glu Tyr Leu His Leu Asn Asp Met Lys Glu
                645                 650                 655

Ala Val Gln Cys Val Gln Glu Leu Ala Ser Pro Ser Leu Leu Phe Ile
                660                 665                 670

Phe Val Arg His Gly Val Glu Ser Thr Leu Glu Arg Ser Ala Ile Ala
                675                 680                 685

Arg Glu His Met Gly Gln Leu Leu His Gln Leu Leu Cys Ala Gly His
        690                 695                 700

Leu Ser Thr Ala Gln Tyr Tyr Gln Gly Leu Tyr Glu Ile Leu Glu Leu
705                 710                 715                 720

Ala Glu Asp Met Glu Ile Asp Ile Pro His Val Trp Leu Tyr Leu Ala
                725                 730                 735

Glu Leu Val Thr Pro Ile Leu Gln Glu Gly Gly Val Pro Met Gly Glu
                740                 745                 750

Leu Phe Arg Glu Ile Thr Lys Pro Leu Arg Pro Leu Gly Lys Ala Ala
        755                 760                 765

Ser Leu Leu Leu Glu Ile Leu Gly Leu Leu Cys Lys Ser Met Gly Pro
770                 775                 780

Lys Lys Val Gly Thr Leu Trp Arg Glu Ala Gly Leu Ser Trp Lys Glu
785                 790                 795                 800

Phe Leu Pro Glu Gly Gln Asp Ile Gly Ala Phe Val Ala Glu Gln Lys
                805                 810                 815

Val Glu Tyr Thr Leu Gly Glu Glu Ser Glu Ala Pro Gly Gln Arg Ala
                820                 825                 830

Leu Pro Ser Glu Glu Leu Asn Arg Gln Leu Glu Lys Leu Leu Lys Glu
        835                 840                 845

Gly Ser Ser Asn Gln Arg Val Phe Asp Trp Ile Glu Ala Asn Leu Ser
850                 855                 860

Glu Gln Gln Ile Val Ser Asn Thr Leu Val Arg Ala Leu Met Thr Ala
865                 870                 875                 880

Val Cys Tyr Ser Ala Ile Ile Phe Glu Thr Pro Leu Arg Val Asp Val
                885                 890                 895

Ala Val Leu Lys Ala Arg Ala Lys Leu Leu Gln Lys Tyr Leu Cys Asp
                900                 905                 910

Glu Gln Lys Glu Leu Gln Ala Leu Tyr Ala Leu Gln Ala Leu Val Val
        915                 920                 925
```

```
Thr Leu Glu Gln Pro Pro Asn Leu Leu Arg Met Phe Phe Asp Ala Leu
    930                 935                 940

Tyr Asp Glu Asp Val Val Lys Glu Asp Ala Phe Tyr Ser Trp Glu Ser
945                 950                 955                 960

Ser Lys Asp Pro Ala Glu Gln Gln Gly Lys Gly Val Ala Leu Lys Ser
                965                 970                 975

Val Thr Ala Phe Phe Lys Trp Leu Arg Glu Ala Glu Glu Ser Asp
                980                 985                 990

His

<210> SEQ ID NO 2
<211> LENGTH: 561
<212> TYPE: PRT
<213> ORGANISM: Arabidopsis thaliana

<400> SEQUENCE: 2

Ala Phe Ala Ser Ser Arg Arg Pro Tyr Leu Ala Asp Phe Ala Arg Cys
1               5                   10                  15

Val Phe His Glu Tyr His Val Cys Ser Phe Ser Phe Gly Glu Val Glu
                20                  25                  30

Asp Pro Phe Leu Trp Asn Ala Val Ile Lys Ser His Ser His Gly Lys
            35                  40                  45

Asp Pro Arg Gln Ala Leu Leu Leu Leu Cys Leu Met Leu Glu Asn Gly
    50                  55                  60

Val Ser Val Asp Lys Phe Ser Leu Ser Leu Val Leu Lys Ala Cys Ser
65                  70                  75                  80

Arg Leu Gly Phe Val Lys Gly Gly Met Gln Ile His Gly Phe Leu Lys
                85                  90                  95

Lys Thr Gly Leu Trp Ser Asp Leu Phe Leu Gln Asn Cys Leu Ile Gly
                100                 105                 110

Leu Tyr Leu Lys Cys Gly Cys Leu Gly Leu Ser Arg Gln Met Phe Asp
            115                 120                 125

Arg Met Pro Lys Arg Asp Ser Val Ser Tyr Asn Ser Met Ile Asp Gly
    130                 135                 140

Tyr Val Lys Cys Gly Leu Ile Val Ser Ala Arg Glu Leu Phe Asp Leu
145                 150                 155                 160

Met Pro Met Glu Met Lys Asn Leu Ile Ser Trp Asn Ser Met Ile Ser
                165                 170                 175

Gly Tyr Ala Gln Thr Ser Asp Gly Val Asp Ile Ala Ser Lys Leu Phe
                180                 185                 190

Ala Asp Met Pro Glu Lys Asp Leu Ile Ser Trp Asn Ser Met Ile Asp
            195                 200                 205

Gly Tyr Val Lys His Gly Arg Ile Glu Asp Ala Lys Gly Leu Phe Asp
    210                 215                 220

Val Met Pro Arg Arg Asp Val Val Thr Trp Ala Thr Met Ile Asp Gly
225                 230                 235                 240

Tyr Ala Lys Leu Gly Phe Val His His Ala Lys Thr Leu Phe Asp Gln
                245                 250                 255

Met Pro His Arg Asp Val Val Ala Tyr Asn Ser Met Met Ala Gly Tyr
                260                 265                 270

Val Gln Asn Lys Tyr His Met Glu Ala Leu Glu Ile Phe Ser Asp Met
            275                 280                 285

Glu Lys Glu Ser His Leu Leu Pro Asp Asp Thr Thr Leu Val Ile Val
    290                 295                 300
```

```
Leu Pro Ala Ile Ala Gln Leu Gly Arg Leu Ser Lys Ala Ile Asp Met
305                 310                 315                 320

His Leu Tyr Ile Val Glu Lys Gln Phe Tyr Leu Gly Gly Lys Leu Gly
            325                 330                 335

Val Ala Leu Ile Asp Met Tyr Ser Lys Cys Gly Ser Ile Gln His Ala
        340                 345                 350

Met Leu Val Phe Glu Gly Ile Glu Asn Lys Ser Ile Asp His Trp Asn
    355                 360                 365

Ala Met Ile Gly Gly Leu Ala Ile His Gly Leu Gly Glu Ser Ala Phe
370                 375                 380

Asp Met Leu Leu Gln Ile Glu Arg Leu Ser Leu Lys Pro Asp Asp Ile
385                 390                 395                 400

Thr Phe Val Gly Val Leu Asn Ala Cys Ser His Ser Gly Leu Val Lys
            405                 410                 415

Glu Gly Leu Leu Cys Phe Glu Leu Met Arg Arg Lys His Lys Ile Glu
        420                 425                 430

Pro Arg Leu Gln His Tyr Gly Cys Met Val Asp Ile Leu Ser Arg Ser
    435                 440                 445

Gly Ser Ile Glu Leu Ala Lys Asn Leu Ile Glu Glu Met Pro Val Glu
450                 455                 460

Pro Asn Asp Val Ile Trp Arg Thr Phe Leu Thr Ala Cys Ser His His
465                 470                 475                 480

Lys Glu Phe Glu Thr Gly Glu Leu Val Ala Lys His Leu Ile Leu Gln
            485                 490                 495

Ala Gly Tyr Asn Pro Ser Ser Tyr Val Leu Leu Ser Asn Met Tyr Ala
        500                 505                 510

Ser Phe Gly Met Trp Lys Asp Val Arg Arg Val Arg Thr Met Met Lys
    515                 520                 525

Glu Arg Lys Ile Glu Lys Ile Pro Gly Cys Ser Trp Ile Glu Leu Asp
530                 535                 540

Gly Arg Val His Glu Phe Phe Val Asp Ser Ile Glu Val Ser Ser Thr
545                 550                 555                 560

Leu

<210> SEQ ID NO 3
<211> LENGTH: 13
<212> TYPE: RNA
<213> ORGANISM: Artificial Sequence
<220> FEATURE:
<223> OTHER INFORMATION: Synthetic RNA

<400> SEQUENCE: 3
uaucuugucu uua                                                              13

<210> SEQ ID NO 4
<211> LENGTH: 12
<212> TYPE: PRT
<213> ORGANISM: Artificial Sequence
<220> FEATURE:
<223> OTHER INFORMATION: Synthetic peptide

<400> SEQUENCE: 4

Met Ala Gly Tyr Pro Tyr Asp Val Pro Asp Tyr Ala
1               5                   10

<210> SEQ ID NO 5
<211> LENGTH: 220
<212> TYPE: PRT
```

<213> ORGANISM: Homo sapiens

<400> SEQUENCE: 5

Met Ala Thr Val Glu Pro Glu Thr Thr Pro Thr Asn Pro Pro Thr
1               5                   10                  15

Thr Glu Glu Lys Thr Glu Ser Asn Gln Glu Val Ala Asn Pro Glu
            20                  25                  30

His Tyr Ile Lys His Pro Leu Gln Asn Arg Trp Ala Leu Trp Phe Phe
        35                  40                  45

Lys Asn Asp Lys Ser Lys Thr Trp Gln Ala Asn Leu Arg Leu Ile Ser
65              55                  60

Lys Phe Asp Thr Val Glu Asp Phe Trp Ala Leu Tyr Asn His Ile Gln
65              70                  75                  80

Leu Ser Ser Asn Leu Met Pro Gly Cys Asp Tyr Ser Leu Phe Lys Asp
                85                  90                  95

Gly Ile Glu Pro Met Leu Glu Asp Glu Lys Asn Lys Arg Gly Gly Arg
            100                 105                 110

Trp Leu Ile Thr Leu Asn Lys Gln Gln Arg Arg Ser Asp Leu Asp Arg
        115                 120                 125

Phe Trp Leu Glu Thr Leu Leu Cys Leu Ile Gly Glu Ser Phe Asp Asp
130                 135                 140

Tyr Ser Asp Asp Val Cys Gly Ala Val Val Asn Val Arg Ala Lys Gly
145                 150                 155                 160

Asp Lys Ile Ala Ile Trp Thr Thr Glu Cys Glu Asn Arg Glu Ala Val
                165                 170                 175

Thr His Ile Gly Arg Val Tyr Lys Glu Arg Leu Gly Leu Pro Pro Lys
            180                 185                 190

Ile Val Ile Gly Tyr Gln Ser His Ala Asp Thr Ala Thr Lys Ser Gly
        195                 200                 205

Ser Thr Thr Lys Asn Arg Phe Val Val Gly Arg Tyr
210                 215                 220

<210> SEQ ID NO 6
<211> LENGTH: 198
<212> TYPE: PRT
<213> ORGANISM: Homo sapiens

<400> SEQUENCE: 6

Met Ala Ala Asp Ile Ser Glu Ser Ser Gly Ala Asp Cys Lys Gly Asp
1               5                   10                  15

Pro Arg Asn Ser Ala Lys Leu Asp Ala Asp Tyr Pro Leu Arg Val Leu
            20                  25                  30

Tyr Cys Gly Val Cys Ser Leu Pro Thr Glu Tyr Cys Glu Tyr Met Pro
        35                  40                  45

Asp Val Ala Lys Cys Arg Gln Trp Leu Glu Lys Asn Phe Pro Asn Glu
50                  55                  60

Phe Ala Lys Leu Thr Val Glu Asn Ser Pro Lys Gln Glu Ala Gly Ile
65              70                  75                  80

Ser Glu Gly Gln Gly Thr Ala Gly Glu Glu Glu Lys Lys Gln
                85                  90                  95

Lys Arg Gly Gly Arg Gly Gln Ile Lys Gln Lys Lys Thr Val Pro
            100                 105                 110

Gln Lys Val Thr Ile Ala Lys Ile Pro Arg Ala Lys Lys Lys Tyr Val
        115                 120                 125

Thr Arg Val Cys Gly Leu Ala Thr Phe Glu Ile Asp Leu Lys Glu Ala

```
                130                 135                 140
Gln Arg Phe Phe Ala Gln Lys Phe Ser Cys Gly Ala Ser Val Thr Gly
145                 150                 155                 160

Glu Asp Glu Ile Ile Ile Gln Gly Asp Phe Thr Asp Ile Ile Asp
                165                 170                 175

Val Ile Gln Glu Lys Trp Pro Glu Val Asp Asp Ser Ile Glu Asp
            180                 185                 190

Leu Gly Glu Val Lys Lys
        195
```

<210> SEQ ID NO 7
<211> LENGTH: 181
<212> TYPE: PRT
<213> ORGANISM: Homo sapiens

<400> SEQUENCE: 7

```
Met Phe Lys Lys Phe Asp Glu Lys Glu Asn Val Ser Asn Cys Ile Gln
1               5                   10                  15

Leu Lys Thr Ser Val Ile Lys Gly Ile Lys Asn Gln Leu Ile Glu Gln
            20                  25                  30

Phe Pro Gly Ile Glu Pro Trp Leu Asn Gln Ile Met Pro Lys Lys Asp
        35                  40                  45

Pro Val Lys Ile Val Arg Cys His Glu His Ile Glu Ile Leu Thr Val
    50                  55                  60

Asn Gly Glu Leu Leu Phe Phe Arg Gln Arg Glu Gly Pro Phe Tyr Pro
65                  70                  75                  80

Thr Leu Arg Leu Leu His Lys Tyr Pro Phe Ile Leu Pro His Gln Gln
                85                  90                  95

Val Asp Lys Gly Ala Ile Lys Phe Val Leu Ser Gly Ala Asn Ile Met
            100                 105                 110

Cys Pro Gly Leu Thr Ser Pro Gly Ala Lys Leu Tyr Pro Ala Ala Val
        115                 120                 125

Asp Thr Ile Val Ala Ile Met Ala Glu Gly Lys Gln His Ala Leu Cys
    130                 135                 140

Val Gly Val Met Lys Met Ser Ala Glu Asp Ile Glu Lys Val Asn Lys
145                 150                 155                 160

Gly Ile Gly Ile Glu Asn Ile His Tyr Leu Asn Asp Gly Leu Trp His
                165                 170                 175

Met Lys Thr Tyr Lys
            180
```

<210> SEQ ID NO 8
<211> LENGTH: 172
<212> TYPE: PRT
<213> ORGANISM: Homo sapiens

<400> SEQUENCE: 8

```
Met Ile Ile Tyr Arg Asp Leu Ile Ser His Asp Glu Met Phe Ser Asp
1               5                   10                  15

Ile Tyr Lys Ile Arg Glu Ile Ala Asp Gly Leu Cys Leu Glu Val Glu
            20                  25                  30

Gly Lys Met Val Ser Arg Thr Glu Gly Asn Ile Asp Ser Leu Ile
        35                  40                  45

Gly Gly Asn Ala Ser Ala Glu Gly Pro Glu Gly Glu Gly Thr Glu Ser
    50                  55                  60

Thr Val Ile Thr Gly Val Asp Ile Val Met Asn His His Leu Gln Glu
```

```
              65                  70                  75                  80
          Thr Ser Phe Thr Lys Glu Ala Tyr Lys Tyr Ile Lys Asp Tyr Met
                          85                  90                  95

Lys Ser Ile Lys Gly Lys Leu Glu Glu Gln Arg Pro Glu Arg Val Lys
                          100                 105                 110

Pro Phe Met Thr Gly Ala Ala Glu Gln Ile Lys His Ile Leu Ala Asn
                          115                 120                 125

Phe Lys Asn Tyr Gln Phe Phe Ile Gly Glu Asn Met Asn Pro Asp Gly
                      130                 135                 140

Met Val Ala Leu Leu Asp Tyr Arg Glu Asp Gly Val Thr Pro Tyr Met
          145                 150                 155                 160

Ile Phe Phe Lys Asp Gly Leu Glu Met Glu Lys Cys
                          165                 170

<210> SEQ ID NO 9
<211> LENGTH: 412
<212> TYPE: PRT
<213> ORGANISM: Homo sapiens

<400> SEQUENCE: 9

Pro Pro Lys Lys Gln Ala Gln Ala Gly Gly Ser Lys Lys Ala Glu Gln
1               5                   10                  15

Lys Lys Lys Glu Lys Ile Ile Glu Asp Lys Thr Phe Gly Leu Lys Asn
                20                  25                  30

Lys Lys Gly Ala Lys Gln Gln Lys Phe Ile Lys Ala Val Thr His Gln
            35                  40                  45

Val Lys Phe Gly Gln Gln Asn Pro Arg Gln Val Ala Gln Ser Glu Ala
    50                  55                  60

Glu Lys Lys Leu Lys Lys Asp Lys Lys Glu Leu Gln Glu Leu
65                  70                  75                  80

Asn Glu Leu Phe Lys Pro Val Ala Ala Gln Lys Ile Ser Lys Gly
                85                  90                  95

Ala Asp Pro Lys Ser Val Val Cys Ala Phe Phe Lys Gln Gly Gln Cys
            100                 105                 110

Thr Lys Gly Asp Lys Cys Lys Phe Ser His Asp Leu Thr Leu Glu Arg
            115                 120                 125

Lys Cys Glu Lys Arg Ser Val Tyr Ile Asp Ala Arg Asp Glu Glu Leu
        130                 135                 140

Glu Lys Asp Thr Met Asp Asn Trp Asp Glu Lys Lys Leu Glu Glu Val
145                 150                 155                 160

Val Asn Lys Lys His Gly Glu Ala Glu Lys Lys Pro Lys Thr Gln
                165                 170                 175

Ile Val Cys Lys His Phe Leu Glu Ala Ile Glu Asn Asn Lys Tyr Gly
            180                 185                 190

Trp Phe Trp Val Cys Pro Gly Gly Asp Ile Cys Met Tyr Arg His
        195                 200                 205

Ala Leu Pro Pro Gly Phe Val Leu Lys Asp Lys Lys Glu Glu
    210                 215                 220

Lys Glu Asp Glu Ile Ser Leu Glu Asp Leu Ile Glu Arg Glu Arg Ser
225                 230                 235                 240

Ala Leu Gly Pro Asn Val Thr Lys Ile Thr Leu Glu Ser Phe Leu Ala
                245                 250                 255

Trp Lys Lys Arg Lys Arg Gln Glu Lys Ile Asp Lys Leu Glu Gln Asp
            260                 265                 270
```

```
Met Glu Arg Arg Lys Ala Asp Phe Lys Ala Gly Lys Ala Leu Val Ile
            275                 280                 285

Ser Gly Arg Glu Val Phe Glu Phe Arg Pro Glu Leu Val Asn Asp Asp
            290                 295                 300

Asp Glu Glu Ala Asp Asp Thr Arg Tyr Thr Gln Gly Thr Gly Gly Asp
305                 310                 315                 320

Glu Val Asp Asp Ser Val Ser Val Asn Asp Ile Asp Leu Ser Leu Tyr
                325                 330                 335

Ile Pro Arg Asp Val Asp Glu Thr Gly Ile Thr Val Ala Ser Leu Glu
            340                 345                 350

Arg Phe Ser Thr Tyr Thr Ser Asp Lys Asp Glu Asn Lys Leu Ser Glu
            355                 360                 365

Ala Ser Gly Gly Arg Ala Glu Asn Gly Glu Arg Ser Asp Leu Glu Glu
            370                 375                 380

Asp Asn Glu Arg Glu Gly Thr Glu Asn Gly Ala Ile Asp Ala Val Pro
385                 390                 395                 400

Val Asp Glu Lys Ser Phe His Trp Arg Gly Phe Gly
            405                 410

<210> SEQ ID NO 10
<211> LENGTH: 269
<212> TYPE: PRT
<213> ORGANISM: Homo sapiens

<400> SEQUENCE: 10

Ala Cys Arg Pro Arg Ser Pro Pro Arg His Gln Ser Arg Cys Asp Gly
1               5                   10                  15

Asp Ala Ser Pro Pro Ser Pro Ala Arg Trp Ser Leu Gly Arg Lys Arg
            20                  25                  30

Arg Ala Asp Gly Arg Arg Trp Arg Pro Glu Asp Ala Glu Glu Ala Glu
        35                  40                  45

His Arg Gly Ala Glu Arg Arg Pro Glu Ser Phe Thr Thr Pro Glu Gly
    50                  55                  60

Pro Lys Pro Arg Ser Arg Cys Ser Asp Trp Ala Ser Ala Val Glu Glu
65              70                  75                  80

Asp Glu Met Arg Thr Arg Val Asn Lys Glu Met Ala Arg Tyr Lys Arg
                85                  90                  95

Lys Leu Leu Ile Asn Asp Phe Gly Arg Glu Arg Lys Ser Ser Ser Gly
            100                 105                 110

Ser Ser Asp Ser Lys Glu Ser Met Ser Thr Val Pro Ala Asp Phe Glu
            115                 120                 125

Thr Asp Glu Ser Val Leu Met Arg Arg Gln Lys Gln Ile Asn Tyr Gly
130                 135                 140

Lys Asn Thr Ile Ala Tyr Asp Arg Tyr Ile Lys Glu Val Pro Arg His
145                 150                 155                 160

Leu Arg Gln Pro Gly Ile His Pro Lys Thr Pro Asn Lys Phe Lys Lys
            165                 170                 175

Tyr Ser Arg Arg Ser Trp Asp Gln Gln Ile Lys Leu Trp Lys Val Ala
            180                 185                 190

Leu His Phe Trp Asp Pro Pro Ala Glu Glu Gly Cys Asp Leu Gln Glu
        195                 200                 205

Ile His Pro Val Asp Leu Glu Ser Ala Glu Ser Ser Ser Glu Pro Gln
    210                 215                 220

Thr Ser Ser Gln Asp Asp Phe Asp Val Tyr Ser Gly Thr Pro Thr Lys
225                 230                 235                 240
```

Val Arg His Met Asp Ser Gln Val Glu Asp Glu Phe Asp Leu Glu Ala
               245                 250                 255

Cys Leu Thr Glu Pro Leu Arg Asp Phe Ser Ala Met Ser
            260                 265

<210> SEQ ID NO 11
<211> LENGTH: 95
<212> TYPE: PRT
<213> ORGANISM: Homo sapiens

<400> SEQUENCE: 11

Pro Gly Pro Thr Pro Ser Gly Thr Asn Val Gly Ser Ser Gly Arg Ser
1               5                   10                  15

Pro Ser Lys Ala Val Ala Arg Ala Ala Gly Ser Thr Val Arg Gln
            20                  25                  30

Arg Lys Asn Ala Ser Cys Gly Thr Arg Ser Ala Gly Arg Thr Thr Ser
        35                  40                  45

Ala Gly Thr Gly Gly Met Trp Arg Phe Tyr Thr Glu Asp Ser Pro Gly
    50                  55                  60

Leu Lys Val Gly Pro Val Pro Val Leu Val Met Ser Leu Leu Phe Ile
65                  70                  75                  80

Ala Ser Val Phe Met Leu His Ile Trp Gly Lys Tyr Thr Arg Ser
                85                  90                  95

<210> SEQ ID NO 12
<211> LENGTH: 23
<212> TYPE: PRT
<213> ORGANISM: Homo sapiens

<400> SEQUENCE: 12

Val Gly Pro Val Pro Val Leu Val Met Ser Leu Leu Phe Ile Ala Ser
1               5                   10                  15

Val Phe Met Leu His Ile Trp
            20

<210> SEQ ID NO 13
<211> LENGTH: 285
<212> TYPE: PRT
<213> ORGANISM: Homo sapiens

<400> SEQUENCE: 13

Arg Leu Leu Pro Arg Leu Leu Leu Leu Leu Val Phe Pro Ala
1               5                   10                  15

Thr Val Leu Phe Arg Gly Gly Pro Arg Gly Leu Leu Ala Val Ala Gln
            20                  25                  30

Asp Leu Thr Glu Asp Glu Glu Thr Val Glu Asp Ser Ile Ile Glu Asp
        35                  40                  45

Glu Asp Asp Glu Ala Glu Val Glu Glu Asp Glu Pro Thr Asp Leu Val
    50                  55                  60

Glu Asp Lys Glu Glu Glu Asp Val Ser Gly Glu Pro Glu Ala Ser Pro
65                  70                  75                  80

Ser Ala Asp Thr Thr Ile Leu Phe Val Lys Gly Glu Asp Phe Pro Ala
                85                  90                  95

Asn Asn Ile Val Lys Phe Leu Val Gly Phe Thr Asn Lys Gly Thr Glu
                100                 105                 110

Asp Phe Ile Val Glu Ser Leu Asp Ala Ser Phe Arg Tyr Pro Gln Asp
            115                 120                 125

```
Tyr Gln Phe Tyr Ile Gln Asn Phe Thr Ala Leu Pro Leu Asn Thr Val
            130                 135                 140

Val Pro Gln Arg Gln Ala Thr Phe Glu Tyr Ser Phe Ile Pro Ala
145                 150                 155                 160

Glu Pro Met Gly Gly Arg Pro Phe Gly Leu Val Ile Asn Leu Asn Tyr
                165                 170                 175

Lys Asp Leu Asn Gly Asn Val Phe Gln Asp Ala Val Phe Asn Gln Thr
                180                 185                 190

Val Thr Val Ile Glu Arg Glu Asp Gly Leu Asp Gly Thr Ile Phe
                195                 200                 205

Met Tyr Met Phe Leu Ala Gly Leu Gly Leu Leu Val Ile Val Gly Leu
210                 215                 220

His Gln Leu Leu Glu Ser Arg Lys Arg Lys Arg Pro Ile Gln Lys Val
225                 230                 235                 240

Glu Met Gly Thr Ser Ser Gln Asn Asp Val Asp Met Ser Trp Ile Pro
                245                 250                 255

Gln Glu Thr Leu Asn Gln Ile Asn Lys Ala Ser Pro Arg Leu Pro
                260                 265                 270

Arg Lys Arg Ala Gln Lys Arg Ser Val Gly Ser Asp Glu
            275                 280                 285

<210> SEQ ID NO 14
<211> LENGTH: 23
<212> TYPE: PRT
<213> ORGANISM: Homo sapiens

<400> SEQUENCE: 14

Thr Ile Phe Met Tyr Met Phe Leu Ala Gly Leu Gly Leu Leu Val Ile
1               5                   10                  15

Val Gly Leu His Gln Leu Leu
            20

<210> SEQ ID NO 15
<211> LENGTH: 609
<212> TYPE: PRT
<213> ORGANISM: Homo sapiens

<400> SEQUENCE: 15

Leu Asp Phe Phe Thr Ile Phe Ser Lys Gly Gly Leu Val Leu Trp Cys
1               5                   10                  15

Phe Gln Gly Val Ser Asp Ser Cys Thr Gly Pro Val Asn Ala Leu Ile
                20                  25                  30

Arg Ser Val Leu Leu Gln Val Gly Phe Gln Lys Ile Leu Thr Leu Thr
            35                  40                  45

Tyr Val Asp Lys Leu Ile Asp Asp Val His Arg Leu Phe Arg Asp Lys
50                  55                  60

Tyr Arg Thr Glu Ile Gln Gln Gln Ser Ala Leu Ser Leu Leu Asn Gly
65                  70                  75                  80

Thr Phe Asp Phe Gln Asn Asp Phe Leu Arg Leu Leu Arg Glu Ala Glu
                85                  90                  95

Glu Ser Ser Lys Ile Arg Ala Pro Thr Thr Met Lys Lys Phe Glu Asp
                100                 105                 110

Ser Glu Lys Ala Lys Lys Pro Val Arg Ser Met Ile Glu Thr Arg Gly
            115                 120                 125

Glu Lys Pro Lys Glu Lys Ala Lys Asn Ser Lys Lys Gly Ala Lys
            130                 135                 140
```

-continued

```
Lys Glu Gly Ser Asp Gly Pro Leu Ala Thr Ser Lys Pro Val Pro Ala
145                 150                 155                 160

Glu Lys Ser Gly Leu Pro Val Gly Pro Glu Asn Gly Val Glu Leu Ser
            165                 170                 175

Lys Glu Glu Leu Ile Arg Arg Lys Arg Glu Glu Phe Ile Gln Lys His
                180                 185                 190

Gly Arg Gly Met Glu Lys Ser Asn Lys Ser Thr Lys Ser Asp Ala Pro
    195                 200                 205

Lys Glu Lys Gly Lys Lys Ala Pro Arg Val Trp Glu Leu Gly Gly Cys
210                 215                 220

Ala Asn Lys Glu Val Leu Asp Tyr Ser Thr Pro Thr Thr Asn Gly Thr
225                 230                 235                 240

Pro Glu Ala Ala Leu Ser Glu Asp Ile Asn Leu Ile Arg Gly Thr Gly
                245                 250                 255

Ser Gly Gly Gln Leu Gln Asp Leu Asp Cys Ser Ser Ser Asp Asp Glu
            260                 265                 270

Gly Ala Ala Gln Asn Ser Thr Lys Pro Ser Ala Thr Lys Gly Thr Leu
        275                 280                 285

Gly Gly Met Phe Gly Met Leu Lys Gly Leu Val Gly Ser Lys Ser Leu
    290                 295                 300

Ser Arg Glu Asp Met Glu Ser Val Leu Asp Lys Met Arg Asp His Leu
305                 310                 315                 320

Ile Ala Lys Asn Val Ala Ala Asp Ile Ala Val Gln Leu Cys Glu Ser
                325                 330                 335

Val Ala Asn Lys Leu Glu Gly Lys Val Met Gly Thr Phe Ser Thr Val
            340                 345                 350

Thr Ser Thr Val Lys Gln Ala Leu Gln Glu Ser Leu Val Gln Ile Leu
        355                 360                 365

Gln Pro Gln Arg Arg Val Asp Met Leu Arg Asp Ile Met Asp Ala Gln
    370                 375                 380

Arg Arg Gln Arg Pro Tyr Val Val Thr Phe Cys Gly Val Asn Gly Val
385                 390                 395                 400

Gly Lys Ser Thr Asn Leu Ala Lys Ile Ser Phe Trp Leu Leu Glu Asn
                405                 410                 415

Gly Phe Ser Val Leu Ile Ala Ala Cys Asp Thr Phe Arg Ala Gly Ala
            420                 425                 430

Val Glu Gln Leu Arg Thr His Thr Arg Arg Leu Ser Ala Leu His Pro
        435                 440                 445

Pro Glu Lys His Gly Gly Arg Thr Met Val Gln Leu Phe Glu Lys Gly
    450                 455                 460

Tyr Gly Lys Asp Ala Ala Gly Ile Ala Met Glu Ala Ile Ala Phe Ala
465                 470                 475                 480

Arg Asn Gln Gly Phe Asp Val Val Leu Val Asp Thr Ala Gly Arg Met
                485                 490                 495

Gln Asp Asn Ala Pro Leu Met Thr Ala Leu Ala Lys Leu Ile Thr Val
            500                 505                 510

Asn Thr Pro Asp Leu Val Leu Phe Val Gly Glu Ala Leu Val Gly Asn
        515                 520                 525

Glu Ala Val Asp Gln Leu Val Lys Phe Asn Arg Ala Leu Ala Asp His
    530                 535                 540

Ser Met Ala Gln Thr Pro Arg Leu Ile Asp Gly Ile Val Leu Thr Lys
545                 550                 555                 560

Phe Asp Thr Ile Asp Asp Lys Val Gly Ala Ala Ile Ser Met Thr Tyr
```

```
                    565                 570                 575

Ile Thr Ser Lys Pro Ile Val Phe Val Gly Thr Gly Gln Thr Tyr Cys
                580                 585                 590

Asp Leu Arg Ser Leu Asn Ala Lys Ala Val Val Ala Ala Leu Met Lys
            595                 600                 605

Ala

<210> SEQ ID NO 16
<211> LENGTH: 18
<212> TYPE: PRT
<213> ORGANISM: Homo sapiens

<400> SEQUENCE: 16

Ser Thr Leu Gly His Met Val Leu Phe Pro Val Trp Phe Leu Tyr Ser
1               5                   10                  15

Leu Leu

<210> SEQ ID NO 17
<211> LENGTH: 261
<212> TYPE: PRT
<213> ORGANISM: Homo sapiens

<400> SEQUENCE: 17

Asp Ile Tyr Asp Thr Gln Thr Leu Gly Val Val Phe Gly Gly Phe
1               5                   10                  15

Met Val Val Ser Ala Ile Gly Ile Phe Leu Val Ser Thr Phe Ser Met
                20                  25                  30

Lys Glu Thr Ser Tyr Glu Glu Ala Leu Ala Asn Gln Arg Lys Glu Met
            35                  40                  45

Ala Lys Thr His His Gln Lys Val Glu Lys Lys Lys Glu Lys Thr
        50                  55                  60

Val Glu Lys Lys Gly Lys Thr Lys Lys Glu Glu Lys Pro Asn Gly
65                  70                  75                  80

Lys Ile Pro Asp His Asp Pro Ala Pro Asn Val Thr Val Leu Leu Arg
                85                  90                  95

Glu Pro Val Arg Ala Pro Ala Val Ala Val Ala Pro Thr Pro Val Gln
            100                 105                 110

Pro Pro Ile Ile Val Ala Pro Val Ala Thr Val Pro Ala Met Pro Gln
        115                 120                 125

Glu Lys Leu Ala Ser Ser Pro Lys Asp Lys Lys Lys Glu Lys Lys
            130                 135                 140

Val Ala Lys Val Glu Pro Ala Val Ser Ser Val Val Asn Ser Ile Gln
145                 150                 155                 160

Val Leu Thr Ser Lys Ala Ala Ile Leu Glu Thr Ala Pro Lys Glu Gly
                165                 170                 175

Arg Asn Thr Asp Val Ala Gln Ser Pro Glu Ala Pro Lys Gln Glu Ala
            180                 185                 190

Pro Ala Lys Lys Lys Ser Gly Ser Lys Lys Gly Pro Pro Asp Ala
        195                 200                 205

Asp Gly Pro Leu Tyr Leu Pro Tyr Lys Thr Leu Val Ser Thr Val Gly
    210                 215                 220

Ser Met Val Phe Asn Glu Gly Glu Ala Gln Arg Leu Ile Glu Ile Leu
225                 230                 235                 240

Ser Glu Lys Ala Gly Ile Ile Gln Asp Thr Trp His Lys Ala Thr Gln
                245                 250                 255
```

```
<210> SEQ ID NO 18
<211> LENGTH: 23
<212> TYPE: PRT
<213> ORGANISM: Homo sapiens

<400> SEQUENCE: 18

Leu Gly Val Val Val Phe Gly Gly Phe Met Val Val Ser Ala Ile Gly
1               5                   10                  15

Ile Phe Leu Val Ser Thr Phe
            20

<210> SEQ ID NO 19
<211> LENGTH: 30
<212> TYPE: PRT
<213> ORGANISM: Homo sapiens

<400> SEQUENCE: 19

Asp Ile Tyr Asp Thr Gln Thr Leu Gly Val Val Val Phe Gly Gly Phe
1               5                   10                  15

Met Val Val Ser Ala Ile Gly Ile Phe Leu Val Ser Thr Phe
            20                  25                  30

<210> SEQ ID NO 20
<211> LENGTH: 4
<212> TYPE: PRT
<213> ORGANISM: Homo sapiens

<400> SEQUENCE: 20

Lys Asp Glu Leu
1

<210> SEQ ID NO 21
<211> LENGTH: 4
<212> TYPE: PRT
<213> ORGANISM: Homo sapiens

<400> SEQUENCE: 21

Lys Glu Glu Leu
1

<210> SEQ ID NO 22
<211> LENGTH: 19
<212> TYPE: PRT
<213> ORGANISM: Homo sapiens

<400> SEQUENCE: 22

Met Gly Trp Ser Cys Ile Ile Leu Phe Leu Val Ala Thr Ala Thr Gly
1               5                   10                  15

Ala His Ser
```